United States Patent
Chang et al.

(10) Patent No.: US 9,321,754 B2
(45) Date of Patent: Apr. 26, 2016

(54) GELATINASE INHIBITORS AND PRODRUGS

(71) Applicants: Mayland Chang, Granger, IN (US); Shahriar Mobashery, Granger, IN (US); Mijoon Lee, Mishawaka, IN (US)

(72) Inventors: Mayland Chang, Granger, IN (US); Shahriar Mobashery, Granger, IN (US); Mijoon Lee, Mishawaka, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 14/567,480

(22) Filed: Dec. 11, 2014

(65) Prior Publication Data
US 2015/0093372 A1      Apr. 2, 2015

Related U.S. Application Data

(62) Division of application No. 13/582,678, filed as application No. PCT/US2011/027282 on Mar. 4, 2011, now Pat. No. 8,937,151.

(60) Provisional application No. 61/310,607, filed on Mar. 4, 2010.

(51) Int. Cl.
| | |
|---|---|
| *A61K 38/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *C07D 409/12* | (2006.01) |
| *C07D 331/02* | (2006.01) |
| *A61K 31/38* | (2006.01) |
| *A61K 38/48* | (2006.01) |
| *A61K 38/49* | (2006.01) |

(52) U.S. Cl.
CPC .............. *C07D 409/12* (2013.01); *A61K 31/38* (2013.01); *A61K 38/482* (2013.01); *A61K 38/4886* (2013.01); *A61K 38/49* (2013.01); *C07D 331/02* (2013.01); *C12Y 304/21* (2013.01); *C12Y 304/21068* (2013.01); *C12Y 304/21073* (2013.01); *C12Y 304/24007* (2013.01); *C12Y 304/24017* (2013.01); *C12Y 304/24023* (2013.01); *C12Y 304/24035* (2013.01)

(58) Field of Classification Search
CPC ............. A61K 38/00; C07K 5/10; C07K 7/06
See application file for complete search history.

(56) References Cited

U.S. PATENT DOCUMENTS

| | | | |
|---|---|---|---|
| 2,965,651 | A | 12/1960 | Milton |
| 4,797,218 | A | 1/1989 | Steinberg et al. |
| 5,288,722 | A | 2/1994 | Kishimoto et al. |
| 5,981,763 | A | 11/1999 | Garapon et al. |
| 6,703,415 | B2 | 3/2004 | Mobashery et al. |
| 7,144,917 | B2 | 12/2006 | Mobashery et al. |
| 7,928,127 | B2 | 4/2011 | Lee et al. |
| 8,093,287 | B2 | 1/2012 | Lee et al. |
| 8,937,151 | B2 | 1/2015 | Chang et al. |

FOREIGN PATENT DOCUMENTS

| | | |
|---|---|---|
| WO | 9535275 | 12/1995 |
| WO | 9718231 | 5/1997 |
| WO | 9833788 A1 | 8/1998 |
| WO | 2006125208 A1 | 11/2006 |
| WO | 2011026107 A1 | 3/2011 |

OTHER PUBLICATIONS

Gooyit et al., "Selective water-soluble gelatinase inhibitor prodrugs," Journal of Medicinal Chemistry (2001) 54: 6676-6690.
Ikejiri et al., "Potent mechanism-based inhibitors for matrix metalloproteinases," The Journal of Biological Chemistry (2005) 280 (40): pp. 33992-34002.
International Search Report and Written Opinion for PCT/US2011/02782 mailed Nov. 4, 2011, 12 pp.
Lee et al., "A potent gelatinase inhibitor with anti-tumor-invasive activity and its metabolic disposition," Chem Biol Drug Des (2009) 73: pp. 189-202.
Testero et al. "Sulfonate-containing thiiranes as selective gelatinase inhibitors," ACS Medical Chemistry Letters (2001) 2: pp. 177-181.

*Primary Examiner* — James H Alstrum Acevedo
*Assistant Examiner* — Kaipeen Yang
(74) *Attorney, Agent, or Firm* — Haukaas Fortius PLLC; Michael H. Haukaas

(57) ABSTRACT

The invention provides compounds, compositions, and methods for the treatment of diseases, disorders, or conditions that are modulated by matrix metalloproteinases (MMPs). The disease, disorder, or condition can include, for example, stroke, neurological disorders, or ophthalmological disorders. The treatment can include administering a compound or composition described herein, thereby providing a prodrug compound that metabolizes to an active MMP inhibitor in vivo. The MMP inhibition can be selective inhibition, for example, selective inhibition of MMP-2, MMP-9, and/or MMP-14. Thus, the invention provides non-mutagenic prodrug compounds of the formulas described herein that result in the inhibition of MMPs upon in vivo administration.

21 Claims, No Drawings

GELATINASE INHIBITORS AND PRODRUGS

RELATED APPLICATIONS

This application is a divisional application of U.S. patent application Ser. No. 13/582,678, filed Sep. 4, 2012, which is a National Stage Application of PCT/US2011/027282, filed Mar. 4, 2011, which claims priority under 35 U.S.C. §119(e) to U.S. Provisional Patent Application No. 61/310,607, filed Mar. 4, 2010, each of which is incorporated herein by reference.

BACKGROUND OF THE INVENTION

Evidence is accumulating that damage to neurons and apoptotic death of neurons play a role in the pathogenesis of many conditions and disorders, including acute and chronic neurologic disorders. These disorders range from acute stroke, head trauma, and epilepsy to more chronic conditions such as Huntington's disease, Alzheimer's disease, HIV-associated dementia, multiple sclerosis, and glaucoma. A contributing factor to several of these diseases is the activation of matrix metalloproteinases (MMPs) in the extracellular matrix.

MMPs constitute a family of extracellular soluble or membrane-bound proteases that are prominently involved in remodeling the extracellular matrix. MMP-9 in particular is significantly elevated in humans after stroke, which is the third leading cause of death in the United States. It is also the primary cause of long-term disability. Acute ischemic stroke, the most common form of stroke, is caused by clotting in the cerebral arteries leading to brain oxygen deprivation and cerebral infarction. Gelatinases (e.g., MMP-2 and MMP-9) are known to be involved in neuronal cell death, blood-brain barrier breakdown and hemorrhage. The only FDA-approved drug for the treatment of ischemic stroke is tissue plasminogen activator (tPA), a thrombolytic agent. The administration of tPA has to be within three hours of the onset of stroke, resulting in its applicability to less than 5% of stroke patients (*CNS Neurol Disord Drug Targets* 2008, 7, 243-53). The use of tPA is also limited by serious side effects, which include neurotoxicity and thrombolysis-associated hemorrhagic transformation, and the use of tPA is contraindicated for patients with evidence of hemorrhage or those who are taking anti-coagulant medication. Blood from stroke patients receiving tPA treatment shows elevated levels of MMP-9, and tPA was shown to activate MMP-9. Additionally, recent reports indicate that tPA upregulates MMP-9 in the brain and contributes to matrix degradation and brain damage.

Accordingly, there is a need for new therapies for the treatment of stroke, and for treatments of stroke that have fewer and/or less severe side effects than currently used therapies. There is also a need for new gelatinase inhibitors, such as selective geleatinase inhibitors, that do not have the side effects of known therapies such as tPa.

SUMMARY

The invention provides a compound of Formula A:

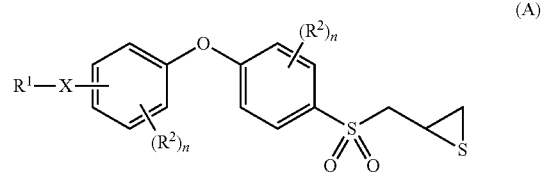

wherein
X is O, —S—NH—, $NR^a$ wherein $R^a$ is H or $(C_1-C_4)$alkyl;
$R^1$ is a solubilizing group comprising 5-30 atoms, in addition to hydrogen, selected from carbon, oxygen, nitrogen, sulfur, and phosphorus, wherein the solubilizing group optionally includes one or more ester, amide, carboxylic acid, phosphate, carbonate, oxime, imine, carbamate, Mannich base (beta-amino ketone), or ether groups;
each $R^2$ is independently H, hydroxy, $(C_1-C_6)$alkyl, $(C_1-C_6)$alkoxy, $(C_1-C_6)$alkanoyl, $(C_1-C_6)$alkanoyloxy, aryl, heteroaryl, carboxy, cyano, nitro, halo, trifluoromethyl, trifluoromethoxy, $SR^z$, $SO_2N(R^z)_2$, $NR^zR^z$, or $COOR^z$; wherein each $R^z$ is independently H, $(C_1-C_6)$alkyl, $(C_1-C_6)$alkanoyl, $(C_6-C_{10})$aroyl, aryl, aryl$(C_1-C_6)$alkyl, heteroaryl, heteroaryl$(C_1-C_6)$alkyl, or optionally a nitrogen protecting group when $R^z$ is covalently bonded to a nitrogen atom; and
each n is independently 0, 1, 2, 3, or 4;
or a salt thereof;
wherein the compound has an aqueous solubility of at least about 5 mg/mL.

In some embodiments, the compound can have an aqueous solubility of at least about 2.5, at least about 5, at least about 7.5, at least about 10, at least about 12.5, at least about 15, at least about 20, at least about 25, at least about 30, or at least about 40 mg/mL. In some embodiments, the compound can have an aqueous solubility of at least 2, 4, 5, 10, 20, 25, or 30 mM. In yet other embodiments, the compound has an aqueous solubility of at least about 4000 times, or at least about 5000 times that of SB-3CT, which has an aqueous solubility of about 2.45 µg/mL.

The compounds of the invention can inhibit matrix metalloproteinases. For example, the compounds can inhibit MMP-2 and have a $K_i$ of less than about 3 µM. In some embodiments, the compound inhibits MMP-9 and has a $K_i$ of less than 20 µM.

The variable group $R^1$—X— can be ortho, meta or para with respect to the phenoxy moiety of Formula A, however, in many embodiments, $R^1$—X— is meta or para with respect to the phenoxy moiety of Formula A.

In some embodiments, X can be O, NH or —S—NH—, n can be 0, and $R^1$ can be:

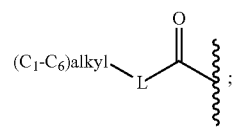

-continued

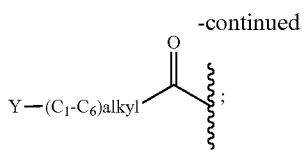

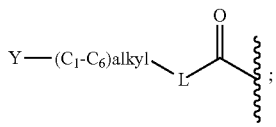

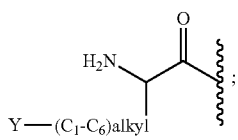

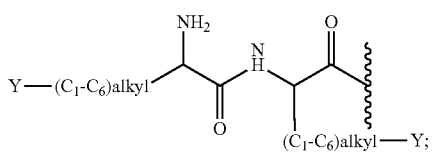

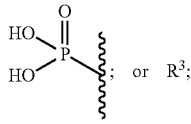 or $R^3$;

wherein
L is O, NH, —OCH$_2$O—, or —C(=O)O—CH$_2$O—;
each Y is independently —NH$_2$, —CO$_2$H, —P(=O)(OH)$_2$, —OP(=O)(OH)$_2$, Het, or a guanidine moiety;
Het is a 5 or 6 membered heterocyclic ring comprising 1, 2, or 3 heteroatoms selected from O, N, S, or P, wherein the ring optionally includes one or two sites of unsaturation and the ring is optionally substituted with 1, 2, or 3 oxo, halo, nitro, or methyl groups; and
$R^3$ is an amino acid or a linear or branched chain of two to five amino acids, linked to X or the carbonyl of $R^1$ by a nitrogen or sulfur atom;
or a salt thereof.

The invention also provides a compound wherein the compound of Formula A is a compound of Formula I:

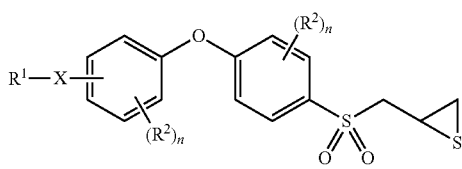

wherein
X is O, NR$^a$, or —S—NH—;
$R^a$ is H or (C$_1$-C$_4$)alkyl;
$R^1$ is —C(=O)-L-(CH$_2$)$_{(m-1)}$—CH$_3$, —(C=O)—(CH$_2$)$_m$—Y; —(C=O)-L-(CH$_2$)$_m$—Y; —(C=O)—(CHR$^x$)—NHR$^y$; —P(=O)(OH)$_2$; an amino acid; or a linear or branched chain of two to five amino acids;
L is O, NH, —OCH$_2$O—, or —C(=O)O—CH$_2$O—;
$R^x$ is H or —(CH$_2$)$_m$Y;
$R^y$ is H or —C(=O)—CH(NH$_2$)—(CH$_2$)$_m$Y;
m is 1-6;
each Y is independently —NH$_2$, —CO$_2$H, —P(=O)(OH)$_2$, —OP(=O)(OH)$_2$, Het, or a guanidine moiety;
Het is a 5 or 6 membered heterocyclic ring comprising 1, 2, or 3 heteroatoms selected from O, N, S, or P, wherein the ring optionally includes one or two sites of unsaturation and the ring is optionally substituted with 1, 2, or 3 oxo, halo, nitro, or methyl groups;
each $R^2$ is independently H, hydroxy, (C$_1$-C$_6$)alkyl, (C$_1$-C$_6$)alkoxy, (C$_1$-C$_6$)alkanoyl, (C$_1$-C$_6$)alkanoyloxy, aryl, heteroaryl, carboxy, cyano, nitro, halo, trifluoromethyl, trifluoromethoxy, SR$^z$, SO$_2$N(R$^z$)$_2$, NR$^z$R$^z$, or COOR$^z$; wherein each R$^z$ is independently H, (C$_1$-C$_6$)alkyl, (C$_1$-C$_6$)alkanoyl, (C$_6$-C$_{10}$)aroyl, aryl, aryl(C$_1$-C$_6$)alkyl, heteroaryl, heteroaryl(C$_1$-C$_6$)alkyl, or optionally a nitrogen protecting group when covalently bonded to a nitrogen atom; and
each n is independently 0, 1, 2, 3, or 4;
or a salt thereof; and
wherein the compound has an aqueous solubility of at least 5 mM.

In some embodiments, X is O or NH, n is 0, and $R^1$ is:

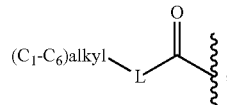

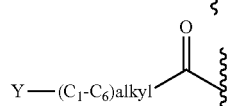

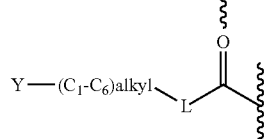

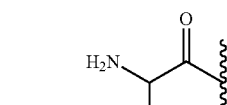

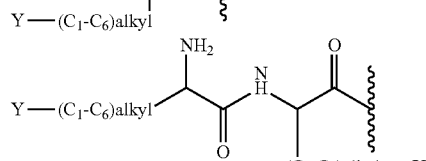

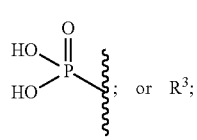 or $R^3$;

wherein
L is O, NH, —OCH$_2$O—, or —C(=O)O—CH$_2$O—;
$R^3$ is an amino acid or a linear or branched chain of two to five amino acids, linked to X by a carbonyl or sulfur residue;
or a salt thereof.

In any embodiment of the invention, each (C$_1$-C$_6$)alkyl can be independently —(CH$_2$)—, —(CH$_2$)$_2$—, —(CH$_2$)$_3$—, —(CH$_2$)$_4$—, —(CH$_2$)$_5$—, or —(CH$_2$)$_6$—.

The invention further provides compounds of the following formulas:

5 6
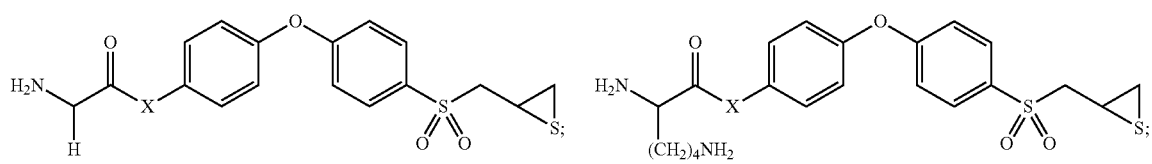
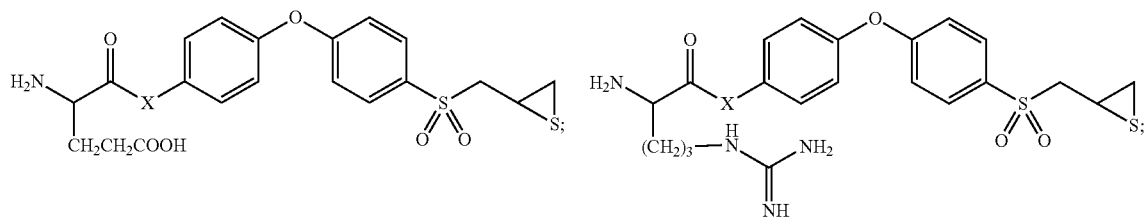
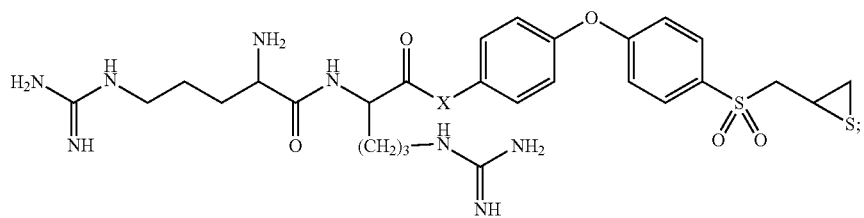
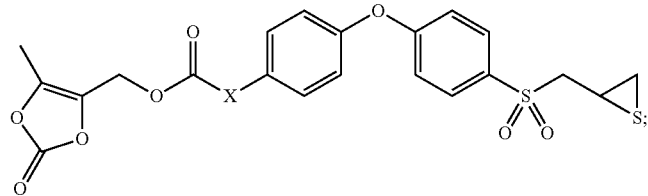
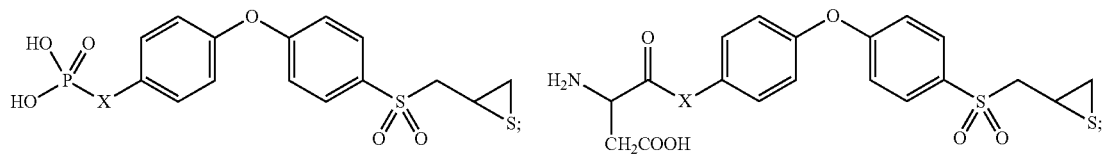
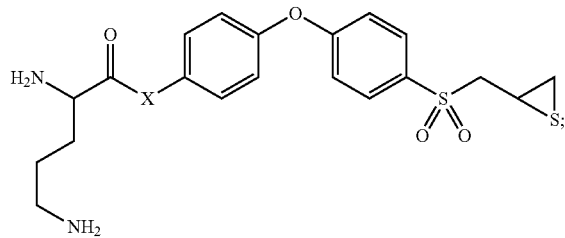
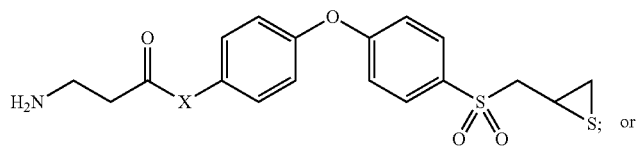
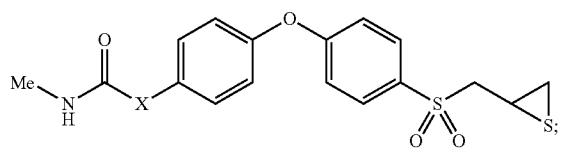

wherein X is O or NH;
or a salt thereof.

Additionally, a compound of Formula I can be a compound of Formula II or Formula III:

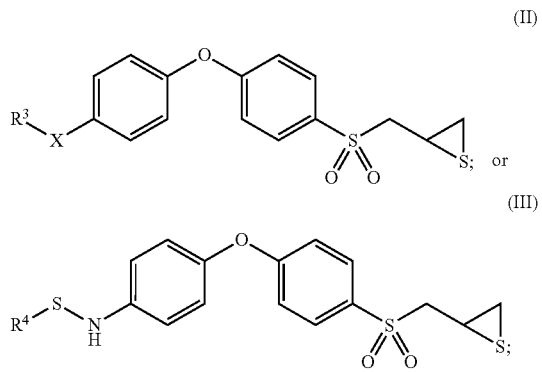

wherein
X is O or NH;
R³ is an amino acid moiety selected from Ala, Cys, Asp, Glu, Phe, Gly, His, Ile, Lys, Leu, Met, Asn, Pro, Gln, Arg, Ser, Thr, Val, Trp, Tyr, or taurine, optionally protected on any nitrogen, sulfur, or carboxylic acid with a protecting group, or a non-natural amino acid, for example, selected from phosphoserine; phosphothreonine; phosphotyrosine; hydroxyproline; γ-carboxyglutamate; hippuric acid; octahydroindole-2-carboxylic acid; statine; 1,2,3,4-tetrahydroisoquinoline-3-carboxylic acid; penicillamine; ornithine; citrulline; α-methylalanine; para-benzoyl-phenylalanine; phenylglycine; propargylglycine; sarcosine; and tert-butylglycine; or
R³ is a combination of any two to five amino acids in a linear or branched configuration; and
R⁴ is a residue of a sulfur-containing amino acid linked to Formula III by its sulfur atom shown as part of Formula III;
or a salt thereof. When the sulfur-containing amino acid linked to Formula III is taurine, the sulfur of Formula III can be the sulfonyl group of taurine (i.e., the sulfur bonded to R⁴ can be a sulfonyl).

The invention additionally provides a pharmaceutical composition comprising a compound of a formula as described herein and a pharmaceutically acceptable diluent or carrier. The pharmaceutical composition can be formulated for intravenous, subcutaneous, intracardiac, intramuscular, intraperatoneal, or topical administration.

Accordingly, the invention provides a method of treating a disease or condition that is modulated by a matrix metalloproteinase (MMP) comprising administering to a patient in need of such treatment an effective amount of a compound of a formula described herein, so that the disease or condition is treated. The matrix metalloproteinase (MMP) can be a gelatinase (e.g., MMP-2, MMP-9, or MMP-13), a collagenase, a stromelysin, MMP-23, MMP-19, or matrilysin, and the activity of the matrix metalloproteinase can be significantly inhibited.

When the compounds, compositions, or methods of the invention are used to inhibit MMPs, the inhibition may be selective for one type of MMP over one or more others. In some embodiments, a compound can selectively inhibit MMP-2, MMP-9, and/or MMP-14. The manner of inhibition may also involve slow-binding inhibition with respect to $k_{on}$ and $k_{off}$ parameters, as documented in Table 2 of Example 2. Accordingly, modulating a matrix metalloproteinase or inhibiting a matrix metalloproteinase includes selectively inhibiting a matrix metalloproteinase, such as MMP-2, MMP-9, and/or MMP-14, while other gelatinases, such as MMP-1, MMP-3, and/or MMP-7 are not inhibited.

The disease or condition can include any disease, disorder, or condition recited herein, including, but not limited to, cancer, stroke, a chronic wound, an ophthalmological disorder, traumatic brain injury, spinal cord injury, subarachnoid hemorrhage, tuberculosis, asthma, glaucoma, retinal ischemia, ischemic optic neuropathy, macular degeneration, sequalae of hyperhomocystinemia, convulsion, pain, aneurism, depression, anxiety, schizophrenia, muscle spasm, migraine headache, urinary incontinence, drug withdrawal, nicotine withdrawal, opiate tolerance or withdrawal, emesis, brain edema, tardive dyskinesia, AIDS-induced dementia, ocular damage, retinopathy, a cognitive disorder, or a neuronal injury associated with HIV-infection; or a gelatinase-mediated neurodegenerative disorder comprising epilepsy, Alzheimer's disease, Huntington's disease, Parkinson's disease, multiple sclerosis, or amyotrophic lateral sclerosis; or a combination thereof.

In some embodiments, the condition is ischemic stroke or hemorrhagic stroke. In another embodiment, the condition is a neurological disorder or ophthalmological disorder. The neurological disorder or ophthalmological disorder can arise from at least one of trauma, ischemic or hypoxic conditions. The neurological disorder can be a neurodegenerative disorder. In some embodiments, the disease, disorder, or condition may arise from at least one of painful neuropathy, neuropathic pain, diabetic neuropathy, drug dependence, drug withdrawal, drug addiction, depression, anxiety, movement disorders, tardive dyskinesia, cerebral infections that disrupt the blood-brain barrier, meningitis, meningoencephalitis, hypoglycemia, cerebral ischemia (stroke), cardiac arrest, spinal cord trauma, head trauma, perinatal hypoxia, or hypoglycemic neuronal damage.

The administering of a compound described herein can be carried out in combination with administering a thrombolytic agent. The thrombolytic agent can be, for example, tissue plasminogen activator (tPA).

The invention provides for the use of a compound described herein to prepare a medicament to treat a disease or condition that is modulated by a matrix metalloproteinase (MMP). The medicament can include a physiologically acceptable diluent or carrier.

The invention thus provides novel compounds of Formula A and Formula I, intermediates for their synthesis, as well as methods of preparing such compounds. The invention also provides compounds of the formulas described herein that are useful as intermediates for the synthesis of other useful compounds. The invention further provides for the use of compounds of Formula A and Formula I for the manufacture of medicaments useful for the treatment of various conditions modulated by matrix metalloproteinases, such as stroke in a mammal.

Additionally, the invention provides compounds and compositions described herein for use in medical therapy. The medical therapy can be treating a neurological disorder or cancer, such as breast cancer, lung cancer, pancreatic cancer, prostate cancer, or colon cancer. Additional diseases, disorders, and conditions that can be treated with such therapy are described herein below. The invention also provides for the use of a compound or composition described herein for the manufacture of a medicament to treat such conditions, for example, conditions in a mammal, such as a human. The medicament can include a pharmaceutically acceptable diluent, excipient, or carrier. The invention further provides for the use of a compound or composition described herein to prepare a medicament for treating such disorders in a mammal, such as a human.

DETAILED DESCRIPTION

The invention may be more fully appreciated by reference to the following description, including the following glossary of terms and the concluding examples. For the sake of brevity, the disclosures of the publications, including patents, cited in this specification are herein incorporated by reference. Reference is herein made to the subject matter recited by certain claims, examples of which are illustrated in the accompanying structures and formulas. While the exemplary subject matter will be described, it will be understood that the exemplary descriptions are not intended to limit the claims. On the contrary, the inventive subject matter is intended to cover all alternatives, modifications, and equivalents, which may be included within the scope of the presently disclosed subject matter as defined by the claims.

INTRODUCTION

The discovery and synthesis of SB-3CT, the first prototype mechanism-based inhibitor for MMPs ($K_i$ 14±1 nM and 600±200 nM for human MMP-2 and MMP-9, respectively) was reported in 2000 (*J. Amer. Chem. Soc.* 2000, 122, 6799-6800; *J. Biol. Chem.* 2000, 275, 41415-23). The $K_i$ values for other MMPs tested in the μM range at best.

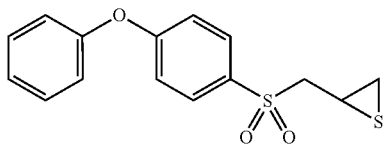

SB-3CT

The selectivity of SB-3CT for inhibition of gelatinases over all other MMPs is due to the ability of gelatinase to facilitate the requisite rate-limiting deprotonation event leading to thiirane-ring opening, giving tight-binding inhibition by the thiolate generated within the active site. SB-3CT was evaluated in a mouse transient ischemia model and found to reduce infarct volume to 30% of control and significantly improved neurobehavioral scores. Notably, administration of SB-3CT at 6 hours after ischemia potently blocked histological damage. Furthermore, SB-3CT has been shown to be effective for the treatment of viral-induced vascular leakage in mice, a model of hemorrhagic fever, and in a rat model of subarachnoid hemorrhage, a type of hemorrhagic stroke. Thus, a selective gelatinase inhibitor can be used for treatment of both ischemic and hemorrhagic stroke.

These studies indicate that MMP-9 and MMP-2 contribute in the disease process of stroke. Gelatinase inhibitors can protect the neurovascular integrity of the brain from ischemia or exogenous tPA thrombolysis by blocking degradation of the basal membrane laminin and exerting anti-apoptotic effects on neurons. Therefore, combined treatment with selective gelatinase inhibitors and tPA can minimize neurotoxicity and hemorrhagic transformation associated with tPA use, thereby extending the window of treatment for reperfusion therapy of tPA.

For this approach to effectively treat stroke patients, it requires delivery of the gelatinase inhibitors by intravenous administration. The prototype selective gelatinase inhibitor SB-3CT has poor aqueous solubility (2.45 μg/mL), therefore it cannot be administered intravenously. In addition, SB-3CT is rapidly metabolized by oxidation at the para position of the terminal phenyl ring and at the α-position with respect to the sulfonyl group. The p-hydroxylated metabolite was a more potent gelatinase inhibitor than the parent SB-3CT ($K_i$ 6±3 nM and 160±80 nM for human MMP-2 and MMP-9, respectively). More than 400 second-generation gelatinase inhibitors have been synthesized that are more water soluble, more metabolically stable, and more potent inhibitors than the parent SB-3CT. These second-generation gelatinase inhibitors contain functional groups that can be used in a prodrug strategy to improve the aqueous solubility and pharmacokinetic properties of the gelatinase inhibitors.

A prodrug (drug+pro-moiety or solubilizing group) is a chemical entity with little or no pharmacological activity that undergoes transformation to the therapeutically active drug in the body. Water-soluble prodrugs of second-generation gelatinase inhibitors have been prepared as described herein. These inhibitors rapidly generate the active drug in the bloodstream. The prodrugs are designed to release naturally occurring non-toxic pro-moieties during the transformation to the therapeutically active drug. The prodrug gelatinase inhibitors are at least 5000-fold more water soluble than SB-3CT and are amenable to intravenous administration. This novel therapeutic strategy by itself or in combination with tPA would reduce injury and extend the time window for thrombolytic therapy in patients with stroke.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a", "an", and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to," "at least," "greater than," "less than," "more than," "or more," and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The terms "comprising", "including", "having", and "composed of" are open-ended terms as used herein.

The term "alkyl" refers to a straight- or branched-chain alkyl group having from 1 to about 20 carbon atoms in the chain. For example, the alkyl group can be a $(C_1-C_{20})$alkyl, a $(C_1-C_2)$alkyl, $(C_1-C_8)$alkyl, $(C_1-C_6)$alkyl, or $(C_1-C_4)$alkyl. Examples of alkyl groups include methyl (Me, which also may be structurally depicted by a/symbol), ethyl (Et), n-propyl, isopropyl, butyl, isobutyl, sec-butyl, tert-butyl (t-Bu), pentyl, isopentyl, tert-pentyl, hexyl, isohexyl, and groups that in light of the ordinary skill in the art and the teachings provided herein would be considered equivalent to any one of the foregoing examples. Alkyl groups can be optionally substituted or unsubstituted, and optionally partially unsaturated, such as in an alkenyl group.

The term "alkenyl" refers to a straight- or branched-chain alkenyl group having from 2 to 20 carbon atoms in the chain. (The double bond of the alkenyl group is formed by two $sp^2$ hybridized carbon atoms.) Illustrative alkenyl groups include $C_1-C_{12}$ alkenyl groups, such as prop-2-enyl, but-2-enyl, but-3-enyl, 2-methylprop-2-enyl, hex-2-enyl, and groups that in light of the ordinary skill in the art and the teachings provided herein would be considered equivalent to any one of the foregoing examples. Alkenyl groups can be optionally substituted or unsubstituted.

The term "cycloalkyl" refers to a saturated or partially saturated, monocyclic, fused polycyclic, or spiro polycyclic carbocycle having from 3 to 12 ring atoms per carbocycle, and can be optionally substituted or unsubstituted. In some embodiments, an alkyl group refers to a cycloalkyl group that accordingly includes a ring structure. Such alkyl groups include (cycloalkyl)-alkyl groups. Illustrative examples of cycloalkyl groups include the following entities, in the form of properly bonded moieties:

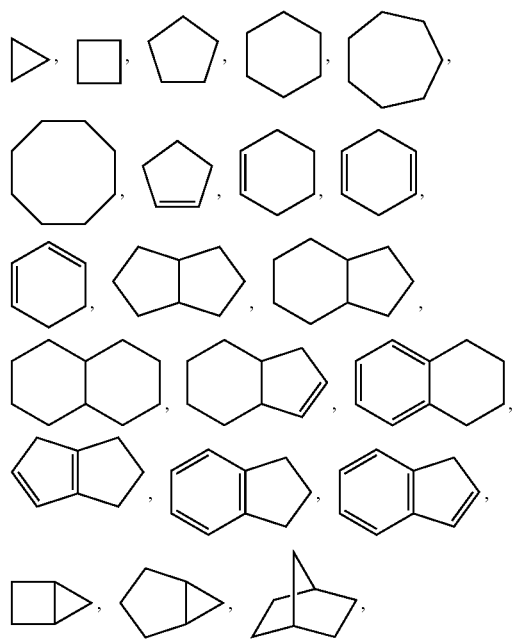

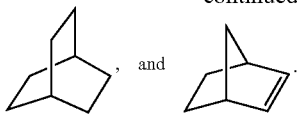

A "heterocycle" or "heterocycloalkyl" group refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members, and can be optionally substituted or unsubstituted. Illustrative examples of heterocycle groups include the following entities, in the form of properly bonded moieties:

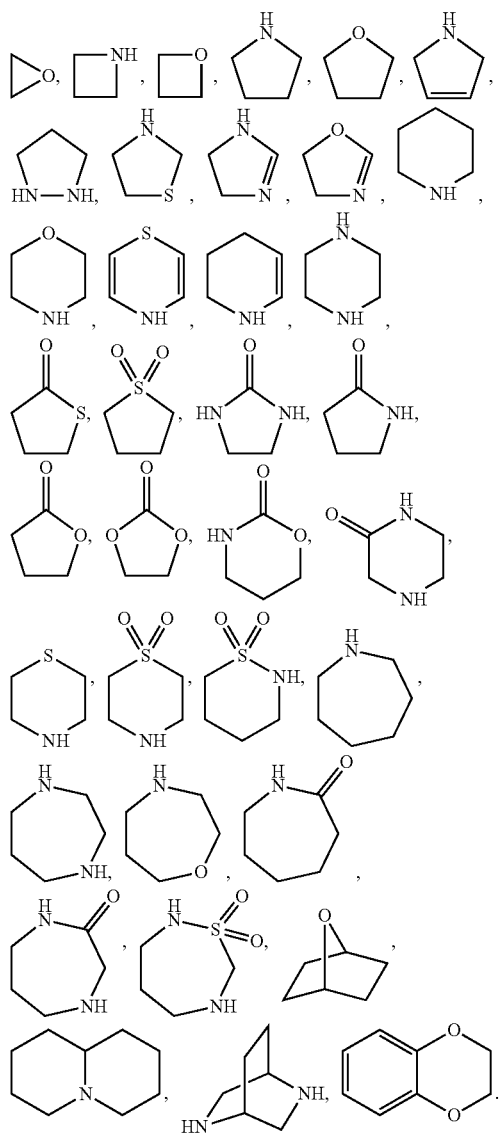

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-14 carbon atoms, about 6-13 carbon atoms, or about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. The heteroaryl can be unsubstituted or optionally substituted. Illustrative examples of heteroaryl groups include the following entities, in the form of properly bonded moieties:

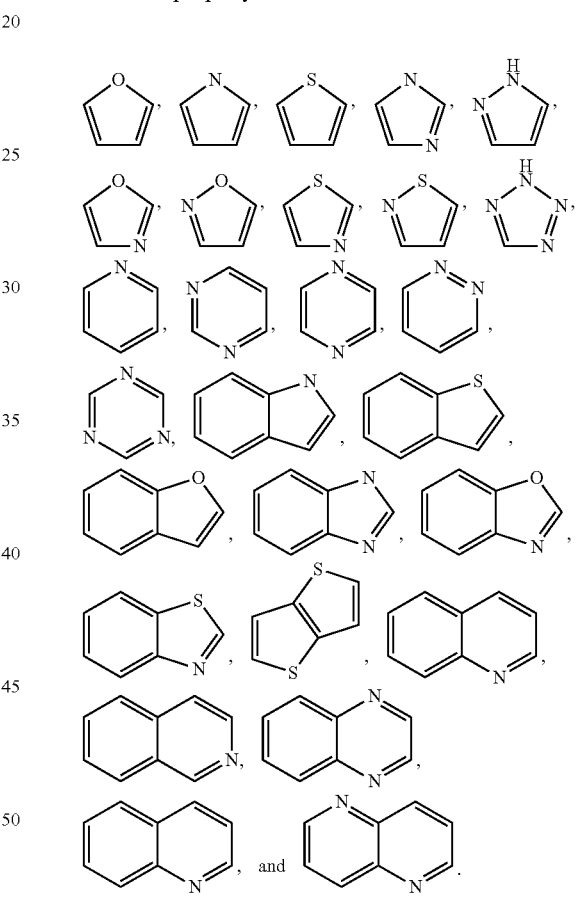

Those skilled in the art will recognize that the species of cycloalkyl, heterocycle, and heteroaryl groups listed or illustrated above are not exhaustive, and that additional species within the scope of these defined terms may also be selected.

As used herein, the term "Het" can refer to a 5 or 6 membered heterocyclic ring comprising 1, 2, or 3 heteroatoms selected from O, N, S, or P, wherein the ring optionally includes one or two cites of unsaturation and the ring is optionally substituted with 1, 2, or 3 oxo, halo, nitro, or methyl groups. The Het group can be a heterocycle group or a heteroaryl group. Examples include oxadiazoles, thiadiazoles, oxazoles, thiazoles, diazines, triazoles, and tetrazoles. In one embodiment, Het specifically refers to 1,3,4-oxadiazoles, 1,2,4-oxadiazoles, the isomeric 1,2,4-oxadiazoles, tetrazoles, 1,3,4-thiadiazoles, oxazoles, 1,2-diazines, thiazoles, and 1,3,4-triazoles. In another specific embodiment, Het specifically refers to 1,2-diazine, a thiazole, a 1,2,4-oxadiazole, a 1,3,4-thiadiazole, a 1,3,4-triazole, or a tetrazole. In yet another embodiment, Het specifically refers to a 1,2,4-oxadiazole, or a 1,3,4-thiadiazole. In other embodiments, Het can refer to a 5-membered heterocyclic ring wherein the ring includes three heteroatoms independently selected from O, S, P, and N. In some embodiments, at least two of the heteroatoms are N. In some embodiments, at least two of the heteroatoms are 0. In yet other embodiments, Het is specifically any 1, 2, 3, 4, 5, 6, 7, or 8 groups selected from 1,3,4-oxadiazoles, 1,2,4-oxadiazoles, the isomeric 1,2,4-oxadiazoles, tetrazoles, 1,3,4-thiadiazoles, oxazoles, 1,2-diazines, thiazoles, and 1,3,4-triazoles.

The term "halogen" represents chlorine, fluorine, bromine or iodine. The term "halo" represents chloro, fluoro, bromo or iodo.

As to any of the groups or "substituents" described herein, each can further include one or more (e.g., 1, 2, 3, 4, 5, or 6) substituents. It is understood, of course, that such groups do not contain any substitution or substitution patterns which are sterically impractical and/or synthetically non-feasible.

The term "substituted" means that a specified group or moiety can bear one or more (e.g., 1, 2, 3, 4, 5, or 6) substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted in some embodiments but can be substituted in other embodiments. Suitable substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl(alkyl)amine, and/or cyano. In certain embodiments, any one of the above groups can be included or excluded from a variable or from a group of substituents.

Specific values listed below for substituents (i.e., groups) and ranges are for illustration only. They do not exclude other defined values or other values within defined ranges for the substituents.

Specifically, $(C_1-C_6)$alkyl can be, for example, methyl, ethyl, propyl, isopropyl, butyl, iso-butyl, sec-butyl, pentyl, 3-pentyl, or hexyl;

$(C_1-C_6)$alkoxy can be methoxy, ethoxy, propoxy, isopropoxy, butoxy, iso-butoxy, sec-butoxy, pentoxy, 3-pentoxy, or hexyloxy;

$(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl;

$(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl;

$(C_1-C_6)$alkanoyl can be acetyl, propanoyl or butanoyl;

$(C_2-C_6)$alkanoyloxy can be acetoxy, propanoyloxy, butanoyloxy, isobutanoyloxy, pentanoyloxy, or hexanoyloxy;

$(C_3-C_8)$cycloalkyl can be cyclopropyl, cyclobutyl, cyclopentyl, cyclohexyl, cycloheptyl, or cyclooctyl;

aryl can be phenyl, indenyl, 5,6,7,8-tetrahydronaphthyl, or naphthyl; and bicyclic aryl can be indenyl or naphthyl.

Het can be heteroaryl, monocyclic heteroaryl, bicyclic heteroaryl, or a non-aromatic heterocycle. Heteroaryl can be furyl, imidazolyl, tetrazolyl, pyridyl (or its N-oxide), thienyl, pyrimidinyl (or its N-oxide), indolyl, or quinolyl (or its N-oxide); monocyclic heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl (or its N-oxide), thienyl, or pyrimidinyl (or its N-oxide); and bicyclic heteroaryl can be quinolyl (or its N-oxide); and bicyclic alkyl can be decahydroquinoline or decahydronaphthalene (cis or trans). The Het group can optionally include, for example, one or two cites of unsaturation, and the ring can optionally be substituted with 1, 2, 3, or 4 substituents, for example, oxo, halo, nitro, or methyl groups.

Any formula given herein is intended to represent compounds having structures depicted by the structural formula as well as certain variations or forms. In particular, compounds of any formula given herein may have asymmetric centers and therefore exist in different enantiomeric and/or diastereomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and/or mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

The invention also specifically includes the racemic, scalemic, R, and S mixtures and forms at the thiirane moiety of compounds of Formula A, Formula I, and their associated formulas. Accordingly, in some embodiments, the stereochemistry of the thiirane chiral center is in the R configuration, and in some embodiments, the stereochemistry of the thiirane chiral center is in the S configuration. Compounds of both configurations actively inhibit MMPs.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively.

Such isotopically labeled compounds are useful in metabolic studies (preferably with $^{14}C$) reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to limit the definition of the moiety for the variable appearing elsewhere. In other words, where a variable appears more than once, the choice of the species from a specified list is independent of the choice of the species for the same variable elsewhere in the formula, or elsewhere in a different formula.

The term "amino acid" includes but is not limited to the following 20 naturally-occurring proteogenic amino acid residues:

| SYMBOL: | DEFINITION | SYMBOL: | DEFINITION |
|---------|------------|---------|------------|
| Ala | Alanine | Met | Methionine |
| Cys | Cysteine | Asn | Asparagine |
| Asp | Aspartic Acid | Pro | Proline |
| Glu | Glutamic Acid | Gln | Glutamine |
| Phe | Phenylalanine | Arg | Arginine |
| Gly | Glycine | Ser | Serine |
| His | Histidine | Thr | Threonine |
| Ile | Isoleucine | Val | Valine |
| Lys | Lysine | Trp | Tryptophan |
| Leu | Leucine | Tyr | Tyrosine |

Thus, an "amino acid" can be a natural amino acid residue (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, taurine, or an unnatural amino acid (e.g., phosphoserine; phosphothreonine; phosphotyrosine; hydroxyproline; gamma-carboxyglutamate; hippuric acid; octahydroindole-2-carboxylic acid; statine; 1,2,3,4-tetrahydroisoquinoline-3-carboxylic acid; penicillamine; ornithine; citrulline; α-methyl-alanine; para-benzoylphenylalanine; phenylglycine; propargylglycine; sarcosine; and tert-butylglycine) residue having one or more open valences. The term also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g., as a ($C_1$-$C_6$)alkyl, phenyl or benzyl ester or amide). Other suitable amino and carboxy protecting groups are known to those skilled in the art (See for example, T. W. Greene, *Protecting Groups In Organic Synthesis*; Wiley: New York, 1981; D. Voet, *Biochemistry, Wiley: New York*, 1990; L. Stryer, *Biochemistry*, (3rd Ed.), W.H. Freeman and Co.: New York, 1975; J. March, *Advanced Organic Chemistry, Reactions, Mechanisms and Structure*, (2nd Ed.), McGraw Hill: New York, 1977; F. Carey and R. Sundberg, *Advanced Organic Chemistry, Part B: Reactions and Synthesis*, (2nd Ed.), Plenum: New York, 1977; and references cited therein). According to the invention, the amino or carboxy protecting group can also comprise a radionuclide (e.g., Fluorine-18, Iodine-123, or Iodine-124).

Modified and protected amino acid residues, as well as peptido-mimetics, are also intended to be encompassed within the definition of "amino acid" or a linear or branched chain of two to five amino acids. As would be readily recognized by one skilled in the art, the amino acid can be linked to the remainder of the compound through its carbonyl residue, its amino residue, or through a sulfur residue if the amino acid includes a thiol group. A linear or branched chain of two to five amino acids can include any combination of two to five Ala, Cys, Asp, Glu, Phe, Gly, His, Ile, Lys, Leu, Met, Asn, Pro, Gln, Arg, Ser, Thr, Val, Trp, or Tyr, optionally protected on nitrogen, sulphur, or a carboxylic acid with protecting groups.

A combination of two to five amino acids can be referred to as a "peptide". A peptide can also be a sequence of 2 to about 10 amino acids (e.g., as defined hereinabove) or peptidic residues having an open valences to link to a formula described herein. The sequence may be linear or cyclic. For example, a cyclic peptide can be prepared or may result from the formation of disulfide bridges between two cysteine residues in a sequence. A peptide can be linked through the carboxy terminus, the amino terminus, or through any other convenient point of attachment, such as, for example, through the sulfur of a cysteine. Peptide derivatives can be prepared as described in U.S. Pat. No. 4,612,302 (Szabo et al.); U.S. Pat. No. 4,853,371 (Coy et al.); and U.S. Pat. No. 4,684,620 (Hruby et al.).

Prodrugs and Metabolites

The invention also relates to pharmaceutically acceptable prodrugs of SB-3CT, and treatment methods using such prodrugs. The term "prodrug" refers to a precursor of a designated compound that, following administration to a subject, yields the compound in vivo via a chemical or physiological process such as solvolysis, enzymatic cleavage, or enzymatic biotransformation, or under physiological conditions (e.g., where a prodrug upon being brought to physiological pH is converted to the compound hydroxy-SB-3CT). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in *Design of Prodrugs*, H. Bundgaard, Ed.; Elsevier, 1985.

Examples of prodrugs include compounds of formula A wherein the solubilizing group is an amino acid residue, or a polypeptide chain of two or more (e.g., two, three or four) amino acid residues, covalently joined through an amide or ester bond to a free amino or hydroxy, such as the hydroxy group of hydroxy-SB-3CT. Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine, methionine sulfone, taurine, and protected versions thereof.

Additional types of a prodrug may be produced, for instance, by derivatizing (chemically converting) the hydroxyl group to an amide or alkyl ester or an amino group to an amide or secondary amine (e.g., thereby providing a 'solubilizing group'). Examples of amides include those derived from ammonia, primary $C_{1-6}$ alkyl amines and secondary di($C_{1-6}$ alkyl)amines. Secondary amines include 5- or 6-membered heterocycloalkyl or heteroaryl ring moieties. Examples of amides include those that are derived from ammonia, $C_{1-3}$ alkyl primary amines, and di($C_{1-2}$ alkyl) amines. Examples of esters of the invention include $C_{1-7}$ alkyl, $C_{5-7}$ cycloalkyl, phenyl, and phenyl($C_{1-6}$ alkyl) esters. Preferred esters include methyl esters. Prodrugs may also be prepared by derivatizing free hydroxy groups using groups including hemisuccinates, phosphate esters, dimethylaminoacetates, and phosphoryloxy-methyloxycarbonyls, following procedures such as those outlined in *Adv. Drug Delivery Rev.* 1996, 19, 115. Carbamate derivatives of hydroxy and amino groups may also yield prodrugs. Suitable transformations well know to those of skill in the art are described by Greg T. Hermanson in *Bioconjugate Techniques*, Academic Press, San Diego, Calif. (1996). Other useful transformations are described in U.S. Patent Publication No. 2009/0005420 (Lee et al.).

Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. These prodrug moieties may incorporate groups including ether, amine, and carboxylic acid functionalities.

The present invention also relates to a method of providing a pharmaceutically active metabolite of a compound of a formula described herein, and uses of such a metabolite in the methods of the invention. A "pharmaceutically active metabolite" refers to a pharmacologically active product of metabolism in the body of a compound of a formula described herein. A prodrug or an active metabolite of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

Compounds and Methods of the Invention

A compound of a formula described herein, or a pharmaceutically acceptable salt thereof, can be administered to a mammal (e.g., human) alone or in conjunction with a second agent, such as a neurological agent, or a pharmaceutically acceptable salt thereof. Accordingly, the compound can be administered in conjunction with a thrombolytic agent, such as tPA to treat a disorder, disease, or condition as described herein.

The term "neurological agent" refers to a compound, including chemical and biological compounds (e.g., peptides, oligonucleotides and antibodies), that has an effect on the nervous system, e.g., compounds capable of treating, inhibiting or preventing disorders affecting the nervous system or compounds capable of eliciting a neurological and/or an ophthalmological disorder or symptoms thereof.

Specific examples of the compounds of Formula A and Formula I include:

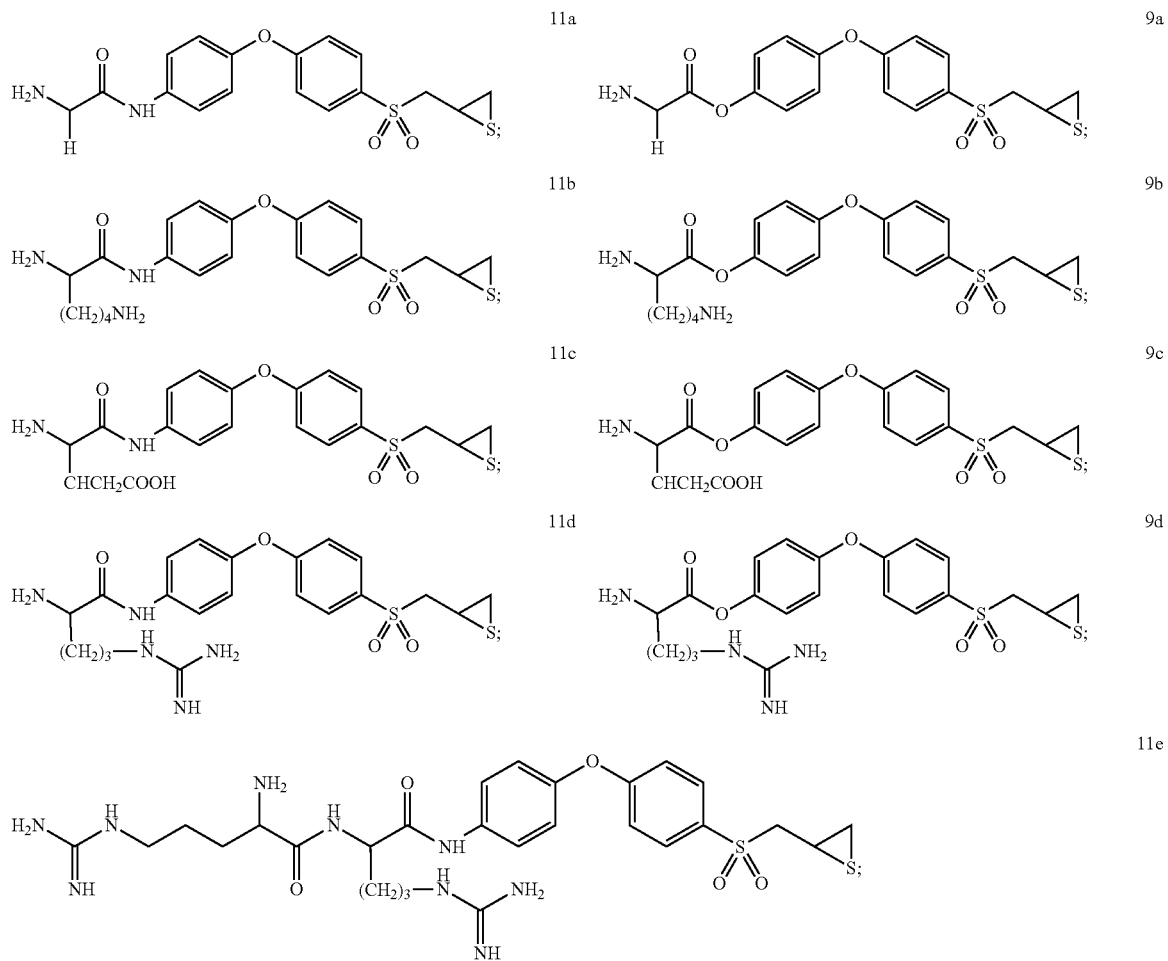

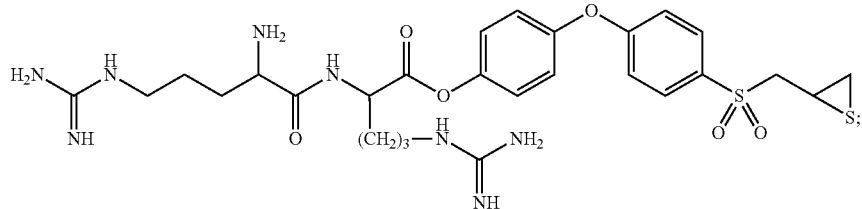
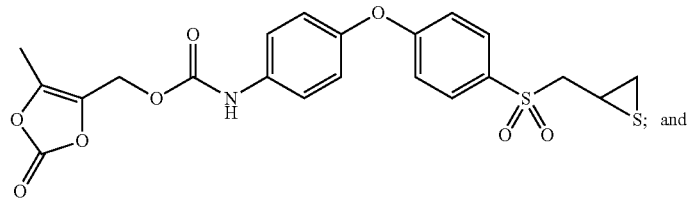
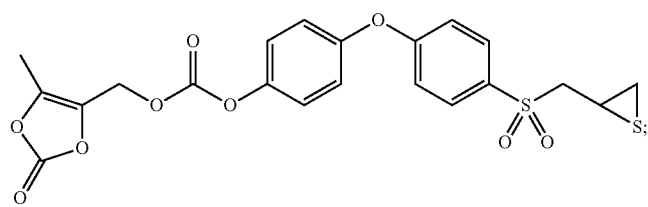
the preparation of which are described in the examples section below. Other compounds of Formula A and Formula I that can be readily prepared using the techniques described herein as well as those well known to those of skill in the art include:
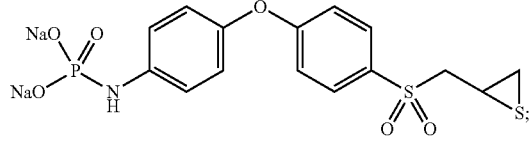
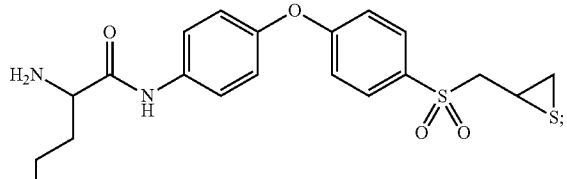
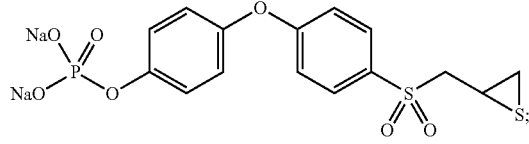
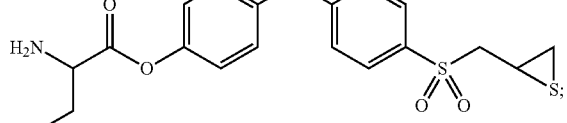
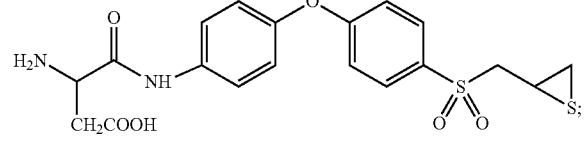
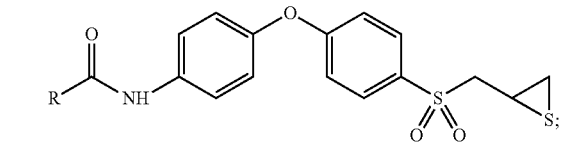
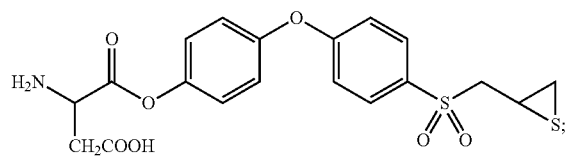
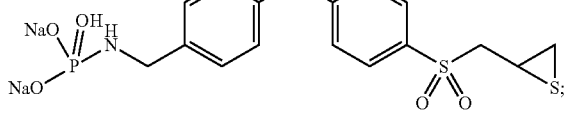

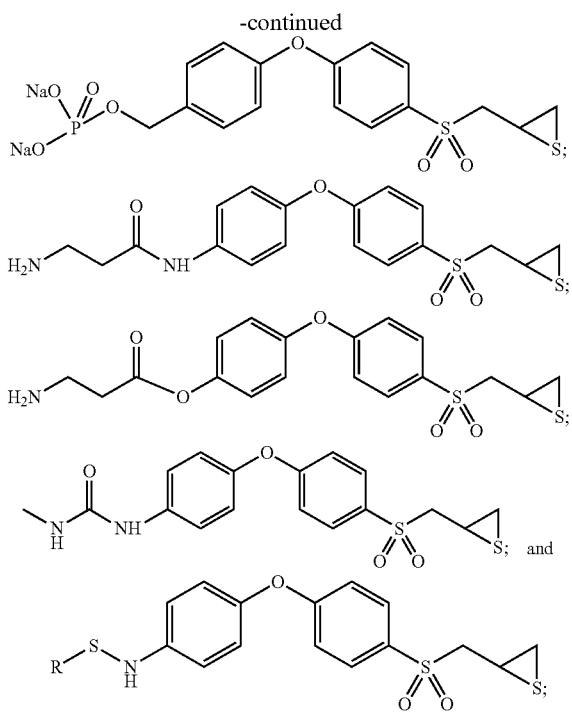

where R is an amino acid or a peptide, such as a linear or branched chain of two to five amino acids. For techniques well known in the art, see for example, March, *Advanced Organic Chemistry, Reactions, Mechanisms and Structure*, 2$^{nd}$ Ed., 1977 and Carey & Sundberg, *Advanced Organic Chemistry, Part B: Reactions*, 2$^{nd}$ Ed., 1983.

Protecting Groups

Compounds of the invention include compounds of Formula A and Formula I, as well as such compounds that also include suitable protecting groups. The term "protecting group" refers to any group that, when bound to a hydroxyl, nitrogen, or other heteroatom prevents undesired reactions from occurring at this group and that can be removed by conventional chemical or enzymatic steps to reestablish the 'unprotected' hydroxyl, nitrogen, or other heteroatom group. The particular removable group employed is often interchangeable with other groups in various synthetic routes. Certain removable protecting groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenyl-silyl (TBDPS), triisopropylsilyl (TIPS), or t-butyldimethylsilyl (TBS)) and any other group that can be introduced chemically onto a hydroxyl functionality and later selectively removed either by chemical or enzymatic methods in mild conditions compatible with the nature of the product.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Greene describes many nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J.; *Protecting Groups* (Georg Thieme Verlag Stuttgart, New York, 1994), which is incorporated herein by reference in its entirety. Some specific protecting groups that can be employed in conjunction with the methods of the invention are discussed below.

Typical nitrogen and oxygen protecting groups described in Greene (pages 14-118) include benzyl ethers, silyl ethers, esters including sulfonic acid esters, carbonates, sulfates, and sulfonates. For example, suitable nitrogen or oxygen protecting groups can include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenylmethyl, tri(p-methoxyphenyl)methyl, 1,3-benzodithiolan-2-yl, benzisothiazolyl S,S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate (mesitoate)); carbonates (methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigolate), o-(methoxycarbonyl)benzoate, p-poly-benzoate, α-naphthoate, nitrate, alkyl N,N,N',N'-tetramethyl-phosphorodiamidate, n-phenylcarbamate, borate, 2,4-dinitrophenylsulfenate); and sulfonates (sulfate, methanesulfonate (mesylate), benzylsulfonate, tosylate, triflate).

Pharmaceutical Salts and Solvates

The invention also includes pharmaceutically acceptable salts and/or solvates of the compounds represented by a formula described herein, such as those described above and of the specific compounds exemplified herein, and methods of treatment using such salts and/or solvates.

A "pharmaceutically acceptable salt" is intended to mean a salt of a free acid or base of a compound represented by a formula described herein that is non-toxic, biologically tolerable, or otherwise biologically suitable for administration to the subject. See, generally, S. M. Berge, et al., "Pharmaceutical Salts", *J. Pharm. Sci.*, 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response.

Pharmaceutically acceptable salts include the addition salts of inorganic acids such as hydrochloride, hydrobromide, hydroiodide, halide, sulfate, phosphate, carbonate, bicarbonate, diphosphate and nitrate or of organic acids such as acetate, malonate, maleate, fumarate, tartrate, succinate, citrate, lactate, benzoate, ascorbate, tosylate, mesylate, trifluoromethanesulphonate, palmoate, stearate, α-ketoglutarate, and α-glycerophosphate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

A compound of a formula described herein may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, behenates, besylates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of a formula described herein contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of a formula described herein includes an acid moiety, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The term "solvate" refers to a solid compound that has one or more solvent molecules associated with its solid structure. Solvates can form when a compound is crystallized from a solvent, wherein one or more solvent molecules become integral part(s) of the crystal. The compounds of a formula described herein can be solvates, for example, ethanol solvates. Likewise, a "hydrate" refers to a solid compound that has one or more water molecules associated with its solid structure. A hydrate is a subgroup of solvates. Hydrates can form when a compound is crystallized from water, wherein one or more water molecules become integral part(s) of the crystal. The compounds of a formula described herein can be hydrates.

Therapeutic Methods

A compound of Formula A or Formula I or a pharmaceutically acceptable salt or solvate thereof, and its pharmaceutically active metabolite (collectively, "active agents") are useful as MMP inhibitors, or for providing MMP inhibitors in vivo, in the methods of the invention. Accordingly, the prodrug compounds described herein can be inactive as MMP inhibitors but can become active agents (inhibitors) in vivo after administration to a patient in need of such treatment. The active agents may be used for the treatment or prevention of medical conditions, diseases, or disorders mediated through inhibition or modulation of various MMPs, such as those described herein. Active agents according to the invention may therefore be used as analgesics, anti-depressants, cognition enhancers, neuroprotectants, sedatives, appetite stimulants, or contraceptives, as well as useful treatments for the conditions described below.

Described herein are numerous diseases and conditions that might appear to be unrelated but each is related by shared mechanistic attributes. Each disease or condition described herein is gelatinase-dependent. For example, both auto-controlled growth and the ability to metastasize are associated with cancer. The prodrug compounds described herein can provide compounds in vivo that are anti-proliferative and are anti-metastatic toward matrix metalloproteinase dependent diseases.

Compounds and pharmaceutical compositions suitable for use in the invention include those wherein the active agent is administered in an effective amount to achieve its intended purpose. The phrase "therapeutically effective amount" refers to an amount effective to treat the disease, disorder, and/or condition, for example, an amount effective to reduce the progression or severity of the condition or symptoms being treated. Determination of a therapeutically effective amount is well within the capacity of persons skilled in the art. The term "effective amount" can include an amount of a compound described herein, or an amount of a combination of compounds described herein, e.g., to treat or prevent a disease or disorder, or to treat the symptoms of the disease or disorder, in a host. Thus, an "effective amount" generally means an amount that provides the desired effect.

The terms "treating", "treat" and "treatment" can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" can include each of medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

Exemplary medical conditions, diseases, and disorders include anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, epilepsy, Niemann-Pick disease, Parkinson's disease, Huntington's chorea, optic neuritis, autoimmune uveitis, symptoms of drug withdrawal, nausea, emesis, sexual dysfunction, post-traumatic stress disorder, or cerebral vasospasm, or combinations thereof, as well as the conditions described below.

The active agents may be used to treat subjects (patients) diagnosed with or suffering from a disease, disorder, or condition that is mediated through MMP activity, e.g., one of the 26 known gelatinases. The term "treat" or "treating" as used herein is intended to refer to administration of an agent or composition of the invention to a subject for the purpose of effecting a therapeutic or prophylactic benefit through modulation of MMP activity. Treating includes reversing, ameliorating, alleviating, inhibiting the progress of, lessening the severity of, or preventing a disease, disorder, or condition, or one or more symptoms of such disease, disorder or condition mediated through modulation of MMP activity.

The term "subject" refers to a mammalian patient in need of such treatment, such as a human. "Modulators" include both inhibitors and activators, where "inhibitors" refer to compounds that decrease, prevent, inactivate, desensitize or down-regulate MMP expression or activity, and "activators" are compounds that increase, activate, facilitate, sensitize, or up-regulate MMP expression or activity.

Accordingly, the invention relates to methods of using the active agents described herein to treat subjects diagnosed with or suffering from a disease, disorder, or condition mediated through MMP activity, such as anxiety, pain, sleep disorders, eating disorders, inflammation, or movement disorders (e.g., multiple sclerosis).

Symptoms or disease states are intended to be included within the scope of "medical conditions, disorders, or diseases." For example, pain may be associated with various diseases, disorders, or conditions, and may include various etiologies. Illustrative types of pain treatable with a MMP-modulating agent according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia.

Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

The invention also provides a composition comprising a compound of any one of the formulas described herein and a pharmaceutically acceptable diluent or carrier. The pharmaceutical composition can include a thrombolytic agent or an analgesic, such as an opioid or a non-steroidal anti-inflammatory drug. Examples of such analgesics include aspirin, acetaminophen, opioids, ibuprofen, naproxen, COX-2 inhibitors, gabapentin, pregabalin, tramadol, or combinations thereof.

The term "thrombolytic agent" refers to a drug that is able to dissolve a clot or "thrombus" and reopen an artery or vein. Thrombolytic agents may be used to treat a heart attack, stroke, deep vein thrombosis (e.g., a clot in a deep leg vein), pulmonary embolism, and occlusion of a peripheral artery or indwelling catheter. Thrombolytic agents are serine proteases and they convert plasminogen to plasmin, which breaks down fibrinogen and fibrin and dissolves blood clots. Currently available thrombolyic agents include reteplase (r-PA or Retavase), alteplase (t-PA or Activase), urokinase (Abbokinase), prourokinase, anisoylated purified streptokinase activator complex (APSAC), and streptokinase. Thrombolytic agents are also called clotbusters, clot-dissolving medications, and fibrinolyic agents.

Accordingly, the invention also provides a method of treating a subject suffering from or diagnosed with a disease, disorder, or medical condition mediated by MMP activity, comprising administering to the subject in need of such treatment an effective amount of at least one compound of a formula described herein, a pharmaceutically acceptable salt thereof, a pharmaceutically acceptable prodrug thereof, or a pharmaceutically active metabolite thereof. The disease, disorder, or medical condition can include anxiety, depression, pain, sleep disorders, eating disorders, inflammation, movement disorders, HIV wasting syndrome, closed head injury, stroke, learning and memory disorders, Alzheimer's disease, epilepsy, Tourette's syndrome, Niemann-Pick disease, Parkinson's disease, Huntington's chorea, optic neuritis, autoimmune uveitis, drug withdrawal, nausea, emesis, sexual dysfunction, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, unwanted pregnancy, hypertension, cancer, hepatitis, allergic airway disease, autoimmune diabetes, intractable pruritus, neuroinflammation, or a combination thereof.

The invention further includes a pharmaceutical composition for treating a disease, disorder, or medical condition mediated by MMP activity, comprising: (a) an effective amount of at least one compound of a formula described herein, or a pharmaceutically acceptable salt, a pharmaceutically acceptable prodrug, or a pharmaceutically active metabolite thereof, or any combination thereof, and a pharmaceutically acceptable excipient. The invention also includes a method of inhibiting fatty acid amide hydrolase activity comprising contacting the fatty acid amide hydrolase with an effective amount of a compound of any one of the formulas described herein. The contacting can be in vivo or in vitro.

The compounds described herein are generally non-mutagenic. The non-mutagenic nature of a compound can be with or without metabolic activation. Mutagenic potential can be evaluated, for example, by measuring a compound's ability to induce reverse mutations at selected loci of Ames II mixed strains and/or strain TA98 in the presence and absence of rat liver S9 metabolic activation (e.g., at concentrations up to 1 mg/mL (equivalent to 300 µM)).

Pharmaceutical Formulations

The compounds described herein can be used to prepare therapeutic pharmaceutical compositions. The compounds may be added to the compositions in the form of a salt or solvate. For example, in cases where compounds are sufficiently basic or acidic to form stable nontoxic acid or base salts, administration of the compounds as salts may be appropriate. Examples of pharmaceutically acceptable salts include organic acid addition salts formed with acids which form a physiological acceptable anion, for example, as described in the section on Pharmaceutical Salts and Solvates. Suitable inorganic salts may also be formed, as described in the section on Pharmaceutical Salts and Solvates.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, or by intravenous, intramuscular, intracardiac, intraperatoneal, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 2% to about 60% of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, *acacia*, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water or saline, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compounds may be applied in pure form, e.g., when they are liquids. However, it will generally be desirable to administer the active agent to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see Jacquet et al. (U.S. Pat. No. 4,608,392), Geria (U.S. Pat. No. 4,992,478), Smith et al. (U.S. Pat. No. 4,559,157), and Wortzman (U.S. Pat. No. 4,820,508). Such dermatological compositions can be used in combinations with the compounds described herein.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

In one embodiment, the invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, breast cancer, colon cancer, lung cancer, prostate cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known.

Combination Therapy

In the following description, component "(b)" is to be understood to represent one or more agents as described herein (e.g., a compound of Formula A or Formula I). Thus, if components (a) and (b) are to be treated the same or independently, each agent of component (b) may also be treated the same or independently. Components (a) and (b) may be formulated together, in a single dosage unit (that is, combined together, e.g., in one lotion, cream, gel, ointment, or formulation for injection) as a combination product. When component (a) and (b) are not formulated together in a single dosage unit, the component (a) may be administered at the same time as component (b), or in any order. For example component (a) may be administered first, followed by administration of component (b), or they may be administered in the reverse order. If component (b) contains more than one agent, e.g., a thrombolytic agent and NSAID, these agents may be administered together or separately in any order. When not administered at the same time, the administration of component (a) and (b) occurs less than about ten hours apart, or about one hour apart in some embodiments.

As is appreciated by a medical practitioner skilled in the art, the dosage of the combination therapy of the invention may vary depending upon various factors such as the pharmacodynamic characteristics of the particular agent and its mode of administration, the age, health and weight of the recipient, the nature and extent of the symptoms, the kind of concurrent treatment, the frequency of treatment, and the effect desired, as described above. The proper dosage of components (a) and (b) will be readily ascertainable by a medical practitioner skilled in the art. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 50-80% relative to the usual dosage of the component when it is administered alone as a single agent for the treatment of a disorder, and related symptoms, in view of synergistic effect of the combination.

Pharmaceutical kits useful for the treatment of disorders described herein, and related symptoms, which include a therapeutically effective amount of a pharmaceutical composition that includes a compound of component (a) and one or more compounds of component (b), in one or more sterile containers, are also within the ambit of the invention. Sterilization of the container may be carried out using conventional sterilization methodology well known to those skilled in the art. Component (a) and component (b) may be in the same sterile container or in separate sterile containers. The sterile containers of materials may include separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

The MMP inhibitor can optionally be co-administered with a neuroprotectant drug, used, for example, in the treatment of Alzheimer's disease or other neurologic or ophthalmologic disorders (e.g., glaucoma), including, but not limited to, memantine or a derivative thereof.

The MMP inhibitor can optionally be co-administered with at least one of the following:

An anti glaucoma agent, beta adrenergic blocking agent, carbonic anhydrase inhibitor, miotic agent, sympathomimetic agent, acetylcholine blocking agent, antihistamine, anti-viral agent, quinolone, anti-inflammatory agent, non-steroidal anti-inflammatory agent, steroidal anti-inflammatory agent, antidepressant (e.g., serotonin reuptake inhibitors, SSRIs), psychotherapeutic agent, anti-anxiety agent, analgesic, antiseizure agent, anti-convulsant, gabapentine, anti-hypertensive agent, benzoporphyrin phtosensitiser, immunosuppressive antimetabolite, anti-convulsant, barbiturate, benzodiazipine, GABA inhibitors, hydantoin, anti-psychotic, neurolaptic, antidysknetic, adrenergic agent, tricyclic antidepressant, anti-hypoglycemic, glucose solution, polypeptide hormone, antibiotic, thrombolytic agent, blood thinner, anti-arrhythmic agent, corticosteroid, seizure disorder agent, anticholinesterase, dopamine blocker, antiparkinsonian agent, muscle relaxant, anxiolytic muscle relaxant, CNS stimulant, antiemetic, beta adrenergic blocking agents, ergot derivative, isometheptene, antiserotonin agent, analgesic, selective serotonin reuptake inhibitors (SSRIs), monoamine oxidase inhibitor, aids adjunct agents, anti infective agent, systemic aids adjunct anti infective, aids chemotherapeutic agent, nucleoside reverse transcriptase, a protease inhibitor, or a thrombolytic agent such as tPA.

Specifically, the MMP inhibitor can optionally be co-administered with at least one of the following:

A beta adrenergic blocking agent, carbonic anhydrase inhibitor, cholinesterase inhibitor, cholinergic (miotic), docosanoid, prostaglandin, tricyclic antidepressant, psychotherapeutic agent, antianxiety agent, analgesic, anti-seizure agent, tricyclic antidepressants having analgesic effect in neuropathic pain, linolenic acid, coenzyme, vitamin, immunosuppressive antimetabolite, antiviral, copolymer, barbiturate, benzodiazepine, GABA inhibitor, hydantoin, tranquilizer, anti-psychotic, norephedrine, peptide, antibacterial, tissue plasminogen activator (TPA), blood thinner/anticoagulant, cardiostimulant, carbonic anhydrase inhibitor, keto-derivative of carbamazepine, acetylcholinesterase, antipsychotic, alkaloid, GABA-B receptor agonist, benzodiazepine, antiparkinsonian, antidepressant, CNS stimulant, receptor antagonist, beta adrenergic blocking agent, ergot derivatives (anti migraine), anticonvulsant, serotonin(5-HT) receptor agonist, antimanic, SSRI, MAOI, aids adjunct anti infective agent, antiviral, and protease inhibitor.

Additionally, the MMP inhibitor can optionally be co-administered with at least one of the following:

Timolol Maleate; Betaxolol HCl; Carteolol HCl; Metipranolol; Timolol Hemihydrate; Brimonidine Tartarate; Brinzolamide; Dorzolamide; Acetazolamide; Echothiophate Iodide; Pilocarpine HCl; Unoprostone Isopropyl ester; Latanoprost; Acamprosate, a drug with additional neuroprotective properties; Amitriptyline; Perphenazine; Chlordiazepoxide; Trimipramine Maleate; Chlodiazepoxide HCl; Alprazolam; Hydroxyzine dihydrochloride; Meprobamate; Doxipin HCl; Hydroxyzine Pamoate; Aspirin; Acetaminophen; Ibuprofen; Carbamazepine; Flupirtine, a drug with neuroprotective properties using additional pathways to MMP antagonists; Lamotrigine; Phenytoin Sodium; Pentaxifylline; Thioctic Acid; Levocarnitine; Biotin; Nicotinic acid; Taurine; Verteporfin; Azathioprine; Interferon Beta 1β, a glycoprotein containing 166 amino acids; Interferon Beta 1α, a glycoprotein containing 166 amino acids; Cyclophosphamide; Methotrexate; Neurmexane, an NMDAR antagonist with improved properties compared to memantine; Glatiramer, an L-Glutamic Acid Polymer with L-alanine, L-lycine, and L-tyrocine; Mephobarbitol; Pentobarbitol; Lorazipam; Clonazepam; Chlorazeptate Dipotassium salt; Fosphenytoin Sodium; Olanzapine; Heloperidol; Trifluoperizine; Fluphenazine; Phenylpropanol amine; Pseudoephedrine HCl; Imipramine; Glucagon; Glucagon-related peptide-1, a 37 amino acid peptide; Glucagon-related peptide-2, a peptide that contains 33 amino acids; Penicilin G, N, O, or V; Ampicillin; Chloramphenicol; Phorbol; Heparin, D-glucosamine with L-iduronic or D-glucuronic acids; Warfarin; Epinephrine; Amiodarone; Lidocaine; Nitroglycerin, isosorbide dinitrate, amyl, butyl, isobutyl or various other nitrates that have been shown to be neuroprotective; Atenolol; Dexamethasone; Prednisolone; Acetazolamide; Phenytoin; Tiagabin HCl; Gabapentin; Oxacarbazepine; Tacrine; Donepezil; Rivastigmine; Heloperidol; Phenothiazine; Reserpine; Tetrabenazene; Bromocryptine; Tiapride; Baclofen; Diazepam; Trihexyphenidyl HCl; Amitrityline; Amphetamines; Methylphenidate; Amitriptylinec; Clomipramine; Dolasetron; Granisetron; Huperzine, an herb used for dementia; Metoclopramide; Prochlorperazine; Dexamethasone; Timolol Hydrogen maleate salt; Propanolol; Isometheptine; Atenolol; Metoprolol; Nadolol; Ergotamine; Dihydroargotamine; Naratriptan; Sumatriptan; Rizatriptan; Zolmitriptan; Imipramine HCl; Dopamine; Clozapine; Valproic Acid; Amitriptylinec; Imipramine HCl; Imipramine Pamoate; Clomipramine; Amphetamine; Methylphenidate; Phenytoin; Phenobarbital; Amitryptyline; Imipramine Pamoate; Nortrityline; Trazodone; Nefazodone; Sertraline; Fluoxetine; Paroxetine; Phenalzine; Tranylcypromine; Erythropoietin, a glycoprotein; Immunoglobulins (gamma globulins); Tetrahydrocannabinols; Alitretinoin; Lamivudin; Stavudin; Zalcitabine; Abacavir; Ritonavir; Indinavir; and Nelfinavir; the chemical names of which are well known in the art and are also described in U.S. Publication No. 2009/0209615 (Liption et al.), which is incorporated herein by reference. Any one or more of the above compounds can be used in a pharmaceutically acceptable salt form, solvate form (e.g., a mono- or di-hydrate), or any combination thereof.

Diseases, Disorders, and Conditions

The term "neurological disorder" refers to any disorder of the nervous system and/or visual system. "Neurological disorders" include disorders that involve the central nervous system (brain, brainstem and cerebellum), the peripheral nervous system (including cranial nerves), and the autonomic nervous system (parts of which are located in both central and peripheral nervous system). Neurodegenerative disorder also refers to a type of neurological disease marked by the loss of nerve cells, including, but not limited to, Alzheimer's disease, Parkinson's disease, amyotrophic lateral sclerosis, tauopathies (including fronto-temporal dementia), and Huntington's disease.

Major groups of neurological disorders include, but are not limited to, headache, stupor and coma, dementia, seizure, sleep disorders, trauma, infections, neoplasms, neuroophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological disorder. The following is a list of several neurological disorders, symptoms, signs and syndromes: Acquired Epileptiform Aphasia; Acute Disseminated Encephalomyelitis; Adrenoleukodystrophy; Agenesis of the corpus callosum; Agnosia; Aicardi syndrome; Alexander disease; Alpers' disease; Alternating hemiplegia; Alzheimer's disease; Amyotrophic lateral sclerosis; Anencephaly; Angelman syndrome; Angiomatosis; Anoxia; Aphasia; Apraxia; Arachnoid Cysts; Arachnoiditis; Arnold-Chiari malformation; Arteriovenous malformation; Asperger syndrome; Ataxia Telangiectasia; Attention Deficit Hyperactivity Disorder; Autism; Autonomic Dysfunction; Back Pain; Batten disease; Behcet's disease; Bell's palsy; Benign Essential Blepharospasm; Benign Focal; Amyotrophy; Benign Intracranial Hypertension; Binswanger's disease; Blepharospasm; Bloch Sulzberger syndrome; Brachial plexus injury; Brain abscess; Brain injury; Brain tumors (including Glioblastoma multiforme); Spinal tumor; Brown-Sequard syndrome; Canavan disease;

Carpal tunnel syndrome (CTS); Causalgia; Central pain syndrome; Central pontine myelinolysis; Cephalic disorder; Cerebral aneurysm; Cerebral arteriosclerosis; Cerebral atrophy; Cerebral gigantism; Cerebral palsy; Charcot-Marie-Tooth disease; Chemotherapy-induced neuropathy and neuropathic pain; Chiari malformation; Chorea; Chronic inflammatory demyelinating polyneuropathy (CIDP); Chronic pain; Chronic regional pain syndrome; Coffin Lowry syndrome; Coma, including Persistent Vegetative State; Congenital facial diplegia; Corticobasal degeneration; Cranial arteritis; Craniosynostosis; Creutzfeldt-Jakob disease; Cumulative trauma disorders; Cushing's syndrome; Cytomegalic inclusion body disease (CIBD); Cytomegalovirus Infection; Dancing eyes-dancing feet syndrome; Dandy-Walker syndrome; Dawson disease; De Morsier's syndrome; Dejerine-Klumpke palsy; Dementia; Dermatomyositis; Diabetic neuropathy; Diffuse sclerosis; Dysautonomia; Dysgraphia; Dyslexia; Dystonias; Early infantile epileptic encephalopathy; Empty sella syndrome; Encephalitis; Encephaloceles; Encephalotrigeminal angiomatosis; Epilepsy; Erb's palsy; Essential tremor; Fabry's disease; Fahr's syndrome; Fainting; Familial spastic paralysis; Febrile seizures; Fisher syndrome; Friedreich's ataxia; Fronto-Temporal Dementia and other "Tauopathies"; Gaucher's disease; Gerstmann's syndrome; Giant cell arteritis; Giant cell inclusion disease; Globoid cell Leukodystrophy; Guillain-Barre syndrome; HTLV-1 associated myelopathy; Hallervorden-Spatz disease; Head injury; Headache; Hemifacial Spasm; Hereditary Spastic Paraplegia; Heredopathia atactica polyneuritiformis; Herpes zoster oticus; Herpes zoster; Hirayama syndrome; HIV-Associated Dementia and Neuropathy (see also Neurological manifestations of AIDS); Holoprosencephaly; Huntington's disease and other polyglutamine repeat diseases; Hydranencephaly; Hydrocephalus; Hypercortisolism; Hypoxia; Immune-Mediated encephalomyelitis; Inclusion body myositis; Incontinentia pigmenti; Infantile; phytanic acid storage disease; Infantile Refsum disease; Infantile spasms; Inflammatory myopathy; Intracranial cyst; Intracranial hypertension; Joubert syndrome; Kearns-Sayre syndrome; Kennedy disease; Kinsbourne syndrome; Klippel Feil syndrome; Krabbe disease; Kugelberg-Welander disease; Kuru; Lafora disease; Lambert-Eaton myasthenic syndrome; Landau-Kleffner syndrome; Lateral medullary (Wallenberg) syndrome; Learning disabilities; Leigh's disease; Lennox-Gastaut syndrome; Lesch-Nyhan syndrome; Leukodystrophy; Lewy body dementia; Lissencephaly; Locked-In syndrome; Lou Gehrig's disease (aka Motor Neuron Disease or Amyotrophic Lateral Sclerosis); Lumbar disc disease; Lyme disease-Neurological Sequelae; Machado-Joseph disease; Macrencephaly; Megalencephaly; Melkersson-Rosenthal syndrome; Menieres disease; Meningitis; Menkes disease; Metachromatic leukodystrophy; Microcephaly; Migraine; Miller Fisher syndrome; Mini-Strokes; Mitochondrial Myopathies; Mobius syndrome; Monomelic amyotrophy; Motor Neurone Disease; Moyamoya disease; Mucopolysaccharidoses; Multi-Infarct Dementia; Multifocal motor neuropathy; Multiple sclerosis and other demyelinating disorders; Multiple system atrophy with postural hypotension; Muscular dystrophy; Myasthenia gravis; Myelinoclastic diffuse sclerosis; Myoclonic encephalopathy of infants; Myoclonus; Myopathy; Myotonia congenital; Narcolepsy; Neurofibromatosis; Neuroleptic malignant syndrome; Neurological manifestations of AIDS; Neurological sequelae of lupus; Neuromyotonia; Neuronal ceroid lipofuscinosis; Neuronal migration disorders; Niemann-Pick disease; O'Sullivan-McLeod syndrome; Occipital Neuralgia; Occult Spinal Dysraphism Sequence; Ohtahara syndrome; Olivopontocerebellar Atrophy; Opsoclonus Myoclonus; Optic neuritis; Orthostatic Hypotension; Overuse syndrome; Paresthesia; Parkinson's disease; Paramyotonia Congenita; Paraneoplastic diseases; Paroxysmal attacks; Parry Romberg syndrome; Pelizaeus-Merzbacher disease; Periodic Paralyses; Peripheral Neuropathy; Painful Neuropathy and Neuropathic Pain; Persistent Vegetative State; Pervasive developmental disorders; Photic sneeze reflex; Phytanic Acid Storage disease; Pick's disease; Pinched Nerve; Pituitary Tumors; Polymyositis; Porencephaly; Post-Polio syndrome; Postherpetic Neuralgia (PHN); Postinfectious Encephalomyelitis; Postural Hypotension; Prader-Willi syndrome; Primary Lateral Sclerosis; Prion diseases; Progressive; Hemifacial Atrophy; Progressive multifocal leukoencephalopathy; Progressive Sclerosing Poliodystrophy; Progressive Supranuclear Palsy; Pseudotumor cerebri; Ramsay-Hunt syndrome (Type I and Type II); Rasmussen's Encephalitis; Reflex Sympathetic Dystrophy syndrome; Refsum disease; Repetitive Motion Disorders; Repetitive Stress Injuries; Restless Legs syndrome; Retrovirus-Associated Myelopathy; Rett syndrome; Reye's syndrome; Saint Vitus Dance; Sandhoff disease; Schilder's disease; Schizencephaly; Septo-Optic Dysplasia; Shaken Baby syndrome; Shingles; Shy-Drager syndrome; Sjogren's syndrome; Sleep Apnea; Soto's syndrome; Spasticity; Spina bifida; Spinal cord injury; Spinal cord tumors; Spinal Muscular Atrophy; Stiff-Person syndrome; Stroke; Sturge-Weber syndrome; Subacute Sclerosing Panencephalitis; Subarachnoid Hemorrhage; Subcortical Arteriosclerotic Encephalopathy; Sydenham Chorea; Syncope; Syringomyelia; Tardive dyskinesia; Tay-Sachs disease; Temporal arteritis; Tethered Spinal Cord syndrome; Thomsen disease; Thoracic Outlet syndrome; Tic Douloureux; Todd's Paralysis; Tourette syndrome; Transient ischemic attack; Transmissible Spongiform Encephalopathies; Transverse myelitis; Traumatic Brain injury; Tremor; Trigeminal Neuralgia; Tropical Spastic Paraparesis; Tuberous Sclerosis; Vascular Dementia (Multi-Infarct Dementia); Vasculitis including Temporal Arteritis; Von Hippel-Lindau Disease (VHL); Wallenberg's syndrome; Werdnig-Hoffman disease; West syndrome; Whiplash; Williams syndrome; Wilson's disease; and Zellweger syndrome.

The term "ophthalmologic disease" or "ophthalmologic disorder" refers to a disease or disorder involving the anatomy and/or function of the visual system, including but not limited to, glaucoma, retinal artery occlusion, ischemic optic neuropathy and wet or dry macular degeneration.

A neurological disorder can be an affective disorder (e.g., depression or anxiety). The term "affective disorder" or "mood disorder" refers to a variety of conditions characterized by a disturbance in mood as the main feature. If mild and occasional, the feelings may be normal. If more severe, they may be a sign of a major depressive disorder or dysthymic reaction or be symptomatic of bipolar disorder. Other mood disorders may be caused by a general medical condition. See, *Mosby's Medical, Nursing & Allied Health Dictionary*, 5th Edition (1998).

The term "depression" refers to an abnormal mood disturbance characterized by feelings of sadness, despair, and discouragement. Depression refers to an abnormal emotional state characterized by exaggerated feelings of sadness, melancholy, dejection, worthlessness, emptiness, and hopelessness, that are inappropriate and out of proportion to reality. See, *Mosby's Medical, Nursing & Allied Health Dictionary*, 5th Edition (1998). Depression can be at least one of a major depressive disorder (single episode, recurrent, mild, moderate, severe without psychotic features, severe with psychotic features, chronic, with catatonic features, with melancholic features, with atypical features, with postpartum onset, in partial remission, in full remission), dysthymic disorder, adjustment disorder with depressed mood, adjustment disorder with mixed anxiety and depressed mood, premenstrual dysphoric disorder, minor depressive disorder, recurrent brief depressive disorder, post-psychotic depressive disorder of schizophrenia, a major depressive disorder associated with Parkinson's disease, and a major depressive disorder associated with dementia.

The term "anxiety disorders" refers to an excessive or inappropriate aroused state characterized by feelings of apprehension, uncertainty, or fear. Anxiety disorders have been classified according to the severity and duration of their symptoms and specific behavioral characteristics. Categories include: Generalized anxiety disorder (GAD), which is long-lasting and low-grade; Panic disorder, which has more dramatic symptoms; Phobias; Obsessive-compulsive disorder (OCD); Post-traumatic stress disorder (PTSD); and Separation anxiety disorder.

The neurological disorder can be pain associated depression (PAD). The term "pain associated depression" refers to a depressive disorder characterized by the co-morbidity of pain and atypical depression. Specifically, the pain can be chronic pain, neuropathic pain, or a combination thereof. Specifically, the pain associated depression can include atypical depression and chronic pain wherein the chronic pain precedes the atypical depression. Alternatively, the pain associated depression can include atypical depression and chronic pain wherein the atypical depression precedes the chronic pain. The pain associated depression can include atypical depression and neuropathic pain.

"Chronic pain" refers to pain that continues or recurs over a prolonged period of time (i.e., >3 mos.), caused by various diseases or abnormal conditions, such as rheumatoid arthritis. Chronic pain may be less intense than acute pain. The person with chronic pain does not usually display increased pulse and rapid perspiration because the automatic reactions to pain cannot be sustained for long periods of time. Others with chronic pain may withdraw from the environment and concentrate solely on their affliction, totally ignoring their family, their friends, and external stimuli. See, *Mosby's Medical, Nursing & Allied Health Dictionary*, 5th Edition (1998).

Chronic pain can be selected from the group of lower back pain, atypical chest pain, headache, pelvic pain, myofascial face pain, abdominal pain, and neck pain or chronic pain is caused by a disease or condition selected from the group of arthritis, temporal mandibular joint dysfunction syndrome, traumatic spinal cord injury, multiple sclerosis, irritable bowel syndrome, chronic fatigue syndrome, premenstrual syndrome, multiple chemical sensitivity, closed head injury, fibromyalgia, rheumatoid arthritis, diabetes, cancer, HIV, interstitial cystitis, migraine headache, tension headache, post-herpetic neuralgia, peripheral nerve injury, causalgia, post-stroke syndrome, phantom limb syndrome, and chronic pelvic pain.

"Atypical depression" refers to a depressed affect, with the ability to feel better temporarily in response to positive life effect (mood reactivity), plus two or more neurovegative symptoms selected from the group of hypersomnia, increased appetite or weight gain, leaden paralysis, and a long standing pattern of extreme sensitivity to perceived interpersonal rejection; wherein the neurovegetative symptoms are present for more than about two weeks. It is appreciated that those of skill in the art recognize that the neurovegatative symptoms can be reversed compared to those found in other depressive disorders (e.g., melancholic depression); hence the term "atypical."

The term "mammal" refers to a class of vertebrate animals of more than 15,000 species, including humans, distinguished by self-regulating body temperature, hair, and in the females, milk-producing mammae. Specifically, mammal can refer to a human. More specifically, mammal can refer to a human adult, e.g., 18 years or older. More specifically, mammal can refer to an elderly human adult, e.g., 60 years or older.

The term "acute neurological disorder" refers to a neurological disorder, as defined above, wherein the disorder has a rapid onset which is followed by a short but severe course, including, but not limited to, Febrile Seizures, Guillain-Barré syndrome, stroke, and intracerebral hemorrhaging (ICH).

The term "chronic neurological disorder" refers to a neurological disorder, as defined above, wherein the disorder lasts for a long period of time (e.g., more than about 2 weeks; specifically, the chronic neurological disorder can continue or recur for more than about 4 weeks, more than about 8 weeks, or more than about 12 weeks) or is marked by frequent recurrence, including, but not limited to, narcolepsy, chronic inflammatory demyelinating polyneuropathy, Cerebral palsy (CP), epilepsy, multiple sclerosis, dyslexia, Alzheimer's disease and Parkinson's Disease.

The term "trauma" refers to any injury or shock to the body, as from violence or an accident. The term trauma also refers to any emotional wound or shock, many of which may create substantial, lasting damage to the psychological development of a person, often leading to neurosis.

The term "ischemic conditions" refers to any condition which results in a decrease in the blood supply to a bodily organ, tissue, or part caused by constriction or obstruction of the blood vessels, often resulting in a reduction of oxygen to the organ, tissue, or part.

The term "hypoxic conditions" refers to conditions in which the amount/concentration of oxygen in the air, blood or tissue is low (subnormal).

The term "painful neuropathy" or "neuropathy" refers to chronic pain that results from damage to or pathological changes of the peripheral or central nervous system. Peripheral neuropathic pain is also referred to as painful neuropathy, nerve pain, sensory peripheral neuropathy, or peripheral neuritis. With neuropathy, the pain is not a symptom of injury, but rather the pain is itself the disease process. Neuropathy is not associated with the healing process. Rather than communicating that there is an injury somewhere, the nerves themselves malfunction and become the cause of pain.

"Neuropathic pain" refers to pain associated with inflammation or degeneration of the peripheral nerves, cranial nerves, spinal nerves, or a combination thereof. The pain is typically sharp, stinging, or stabbing. The underlying disorder can result in the destruction of peripheral nerve tissue and can be accompanied by changes in the skin color, temperature, and edema. See, *Mosby's Medical, Nursing & Allied Health Dictionary*, 5th Edition (1998); and *Stedman's Medical Dictionary*, 25th Edition (1990).

The term "diabetic neuropathy" refers to a peripheral nerve disorder/nerve damage caused by diabetes, including peripheral, autonomic, and cranial nerve disorders/damage associated with diabetes. Diabetic neuropathy refers to a common complication of diabetes mellitus in which nerves are damaged as a result of hyperglycemia (high blood sugar levels).

The term "drug dependence" refers to habituation to, abuse of, and/or addiction to a chemical substance. Largely because of psychological craving, the life of the drug-dependent person revolves around the need for the specific effect of one or more chemical agents on mood or state of consciousness. The term thus includes not only the addiction (which emphasizes the physiological dependence) but also drug abuse (in which the pathological craving for drugs seems unrelated to physical dependence). Examples include, but are not limited to, alcohol, opiates, synthetic analgesics with morphine-like effects, barbiturates, hypnotics, sedatives, some antianxiety agents, cocaine, psychostimulants, marijuana, nicotine and psychotomimetic drugs.

The term "drug withdrawal" refers to the termination of drug taking Drug withdrawal also refers to the clinical syndrome of psychological, and, sometimes physical factors that result from the sustained use of a particular drug when the drug is abruptly withdrawn. Symptoms are variable but may include anxiety, nervousness, irritability, sweating, nausea, vomiting, rapid heart rate, rapid breathing, and seizures.

The term "drug addiction" or dependence is defined as having one or more of the of the following signs: a tolerance for the drug (needing increased amounts to achieve the same effect), withdrawal symptoms, taking the drug in larger amounts than was intended or over a longer period of time than was intended, having a persistent desire to decrease or the inability to decrease the amount of the drug consumed, spending a great deal of time attempting to acquire the drug, or continuing to use the drug even though the person knows there are reoccurring physical or psychological problems being caused by the drug.

In one embodiment, when treating drug withdrawal, dependence and/or tolerance, the MMP inhibitor is administered with an NMDAR antagonist (e.g., memantine).

The term "tardive dyskinesia" refers to a serious, irreversible neurological disorder that can appear at any age. Tardive Dyskinesia, e.g., Tourette's syndrome, can be a side effect of long-term use of antipsychotic/neuroleptic drugs. Symptoms can be hardly noticeable or profound. Symptoms involve uncontrollable movement of various body parts, including the body trunk, legs, arms, fingers, mouth, lips, or tongue.

The term "movement disorder" refers to a group of neurological disorders that involve the motor and movement systems, including, but are not limited to, Ataxia, Parkinson's disease, Blepharospasm, Angelman Syndrome, Ataxia Telangiectasia, Dysphonia, Dystonic disorders, Gait disorders, Torticollis, Writer's Cramp, Progressive Supranuclear Palsy, Huntington's Chorea, Wilson's Disease, Myoclonus, Spasticity, Tardive dyskinesia, Tics and Tourette syndrome and Tremors.

The term "cerebral infections that disrupt the blood-brain barrier" refers to infections of the brain or cerebrum that result in an alteration in the effectiveness of the blood-brain barrier, either increasing or decreasing its ability to prevent, for example, substances and/or organisms from passing out of the bloodstream and into the CNS.

The term "the blood-brain barrier" refers to a semi-permeable cell layer of endothelial cells (interior walls) within capillaries of the central nervous system (CNS). The blood-brain barrier prevents large molecules, immune cells, many potentially damaging substances, and foreign organisms (e.g., viruses), from passing out of the bloodstream and into the CNS (Brain and Spinal Cord). A dysfunction in the Blood-Brain Barrier may underlie in part the disease process in MS (multiple sclerosis).

The term "meningitis" refers to inflammation of the meninges of the brain and the spinal cord, most often caused by a bacterial or viral infection and characterized by fever, vomiting, intense headache, and stiff neck.

The term "meningoencephalitis" refers to inflammation of both the brain and meninges.

The term "stroke" refers to a sudden loss of brain function caused by a blockage or rupture of a blood vessel to the brain (resulting in the lack of oxygen to the brain), characterized by loss of muscular control, diminution or loss of sensation or consciousness, dizziness, slurred speech, or other symptoms that vary with the extent and severity of the damage to the brain, also called cerebral accident, or cerebrovascular accident. The term "cerebral ischemia" (or "stroke") also refers to a deficiency in blood supply to the brain, often resulting in a lack of oxygen to the brain.

The term "hypoglycemia" refers to an abnormally low level of glucose in the blood.

The term "cardiac arrest" refers to a sudden cessation of heartbeat and cardiac function, resulting in a temporary or permanent loss of effective circulation.

The term "spinal cord trauma" refers to damage to the spinal cord that results from direct injury to the spinal cord itself or indirectly by damage to the bones and soft tissues and vessels surrounding the spinal cord. It is also called Spinal cord compression; Spinal cord injury; or Compression of spinal cord.

The term "head trauma" refers to a head injury of the scalp, skull, or brain. These injuries can range from a minor bump on the skull to a devastating brain injury. Head trauma can be classified as either closed or penetrating. In a closed head injury, the head sustains a blunt force by striking against an object. A concussion is a type of closed head injury that involves the brain. In a penetrating head injury, an object breaks through the skull and enters the brain.

The term "perinatal hypoxia" refers to a lack of oxygen during the perinatal period (defined as the period of time occurring shortly before and after birth, variously defined as beginning with completion of the twentieth to twenty eighth week of gestation and ending 7 to 28 days after birth).

The term "hypoglycemic neuronal damage" refers to neuronal damage, for example, nerve damage, as a result of a hypoglycemic condition (an abnormally low level of glucose in the blood).

The term "epilepsy" refers to any of various neurological disorders characterized by sudden recurring attacks of motor, sensory, or psychic malfunction with or without loss of consciousness or convulsive seizures.

The term "Alzheimer's disease" refers to a disease marked by the loss of cognitive ability, generally over a period of 10 to 15 years, and associated with the development of abnormal tissues and protein deposits in the cerebral cortex (known as plaques and tangles).

The term "Huntington's disease" refers to a disease that is hereditary in nature and develops in adulthood and ends in dementia. More specifically, Huntington's disease (HD) results from genetically programmed degeneration of brain cells, called neurons, in certain areas of the brain caused by a polyglutamine repeat in the DNA sequence of the gene encoding the protein huntingtin. This degeneration causes uncontrolled movements, loss of intellectual faculties, and emotional disturbance.

The term "Parkinsonism" refers to a disorder similar to Parkinson's disease, but which is caused by the effects of a medication, a different neurodegenerative disorder or another illness. The term "parkinsonism" also refers to any condition that causes any combination of the types of movement abnormalities seen in Parkinson's disease by damaging or destroying dopamine neurons in a certain area of the brain.

The term "amyotrophic lateral sclerosis" (ALS), also called Lou Gehrig's disease and Motor Neuron Disease, refers to a progressive, fatal neurological disease. The disorder belongs to a class of disorders known as motor neuron diseases. ALS occurs when specific nerve cells in the brain and spinal cord that control voluntary movement gradually degenerate (usually the "upper" (in the cerebrocortex) and "lower" (in the spinal cord) motor neurons, although some variants known as primary lateral sclerosis, apparently representing a separate disease, affect only the upper motor neurons). The loss of these motor neurons causes the muscles under their control to weaken and waste away, leading to paralysis. ALS manifests itself in different ways, depending on which muscles weaken first. Symptoms may include tripping and falling, loss of motor control in hands and arms, difficulty speaking, swallowing and/or breathing, persistent fatigue, and twitching and cramping, sometimes quite severely. Upper motor neuron variants (e.g., primary lateral sclerosis) are also included.

The term "glaucoma" refers to any of a group of eye diseases characterized by abnormally high intraocular fluid pressure, damaged optic disk, hardening of the eyeball, and partial to complete loss of vision. The retinal ganglion cells are lost in glaucoma. Some variants of glaucoma have normal intraocular pressure (known also as low tension glaucoma).

The term "retinal ischemia" refers to a decrease in the blood supply to the retina.

The term "ischemic optic neuropathy" refers to a condition that usually presents with sudden onset of unilaterally reduced vision. The condition is the result of decreased blood flow to the optic nerve (ischemia). There are two basic types: arteritic and non-arteritic ischemic optic neuropathy. Non-arteritic ischemic optic neuropathy is generally the result of cardiovascular disease. Those patients at greatest risk have a history of high blood pressure, elevated cholesterol, smoking, diabetes, or combinations of these. Arteritic ischemic optic neuropathy is a condition caused by the inflammation of vessels supplying blood to the optic nerve, known as temporal arteritis. This condition usually presents with sudden and severe vision loss in one eye, pain in the jaw with chewing, tenderness in the temple area, loss of appetite, and a generalized feeling of fatigue or illness.

The term "macular degeneration" refers to the physical disturbance of the center of the retina called the macula. The macula is the part of the retina which is capable of our most acute and detailed vision. Macular degeneration is the leading cause of legal blindness in people over age 55 (legal blindness means that a person can see 20/200 or less with eyeglasses.) Even with a loss of central vision, however, color vision and peripheral vision may remain clear. Vision loss usually occurs gradually and typically affects both eyes at different rates.

As used herein a "demyelinating disorder" refers to a medical condition where the myelin sheath is damaged. The myelin sheath surrounds nerves and is responsible for the transmission of impulses to the brain. Damage to the myelin sheath may result in muscle weakness, poor coordination and possible paralysis. Examples of demyelinating disorders include Multiple Sclerosis (MS), optic neuritis, transverse neuritis and Guillain-Barre Syndrome (GBS). In one embodiment, when treating a demyelinating disorder, an MMP inhibitor is administered with an NMDAR antagonist (e.g., memantine) or with β-interferon isoforms, copaxone or Antegren (natalizumab). Recently, it has been noted that underlying neuronal damage can occur in demyelinating conditions such as MS, and therefore useful drugs may also protect the neurons instead or in addition to the myelin.

The term "multiple sclerosis" refers to a chronic disease of the central nervous system, which predominantly affects young adults. Viral and autoimmune etiologies are postulated. Genetic and environmental factors are known to contribute to MS, but a specific cause for this disease is not yet identified. Pathologically, MS is characterized by the presence of areas of demyelination and T-cell predominant perivascular inflammation in the brain white matter. Some axons may be spared from these pathological processes. The disease begins most commonly with acute or subacute onset of neurologic abnormalities. Initial and subsequent symptoms may dramatically vary in their expression and severity over the course of the disease, that usually lasts for many years. Early symptoms may include numbness and/or paresthesia, mono- or paraparesis, double vision, optic neuritis, ataxia, and bladder control problems. Subsequent symptoms also include more prominent upper motor neuron signs, i.e., increased spasticity, increasing para- or quadriparesis. Vertigo, incoordination and other cerebellar problems, depression, emotional lability, abnormalities in gait, dysarthria, fatigue and pain are also commonly seen.

The term "sequelae of hyperhomocystinemia" refers to a condition following as a consequence hyperhomocystinemia, meaning elevated levels of homocysteine.

The term "convulsion" refers to a violent involuntary contraction or series of contractions of the muscles.

The term "pain" refers to an unpleasant sensation associated with actual or potential tissue damage, and mediated by specific nerve fibers to the brain where its conscious appreciation may be modified by various factors. See, *Mosby's Medical, Nursing & Allied Health Dictionary*, 5$^{th}$ Ed. (1998); and *Stedman's Medical Dictionary*, 25$^{th}$ Ed. (1990).

The term "anxiety" refers to a state of apprehension, uncertainty, and/or fear resulting from the anticipation of a realistic or fantasized threatening event or situation, often impairing physical and psychological functioning.

The term "schizophrenia" refers to any of a group of psychotic disorders usually characterized by withdrawal from reality, illogical patterns of thinking, delusions, and hallucinations, and accompanied in varying degrees by other emotional, behavioral, or intellectual disturbances. Schizophrenia is associated with dopamine imbalances in the brain and defects of the frontal lobe and is caused by genetic, other biological, and/or psychosocial factors.

The term "muscle spasm" refers to an often painful involuntary muscular contraction The term "migraine headache" refers to a severe, debilitating headache often associated with photophobia and blurred vision.

The term "urinary incontinence" refers to the inability to control the flow of urine and involuntary urination.

The term "nicotine withdrawal" refers to the withdrawal from nicotine, an addictive drug found in tobacco, which is characterized by symptoms that include headache, anxiety, nausea and a craving for more tobacco. Nicotine creates a chemical dependency, so that the body develops a need for a certain level of nicotine at all times. Unless that level is maintained, the body will begin to go through withdrawal. For tobacco users trying to quit, symptoms of withdrawal from nicotine are unpleasant and stressful, but temporary. Most withdrawal symptoms peak 48 hours after one quits and are completely gone in six months.

The term "opiate tolerance" can be explained, at least in part, as a homeostatic response that reduces the sensitivity of the system to compensate for continued exposure to high levels of, for example, morphine or heroin. When the drug is stopped, the system is no longer as sensitive to the soothing effects of the enkephalin neurons and the pain of withdrawal is produced.

The term "opiate withdrawal" refers to an acute state caused by cessation or dramatic reduction of use of opiate drugs that has been heavy and prolonged (several weeks or longer). Opiates include heroin, morphine, codeine, Oxycontin, Dilaudid, methadone, and others. The reaction frequently includes sweating, shaking, headache, drug craving, nausea, vomiting, abdominal cramping, diarrhea, inability to sleep, confusion, agitation, depression, anxiety, and other behavioral changes.

The term "emesis" refers to the act of vomiting.

The term "brain edema" refers to an excessive accumulation of fluid in, on, around and/or in relation to the brain.

The term "AIDS induced dementia" or "HIV-associated dementia" refers to dementia (deterioration of intellectual faculties, such as memory, concentration, and judgment, resulting from an organic disease or a disorder of the brain) induced by AIDS (Acquired Immunodeficiency Syndrome—an epidemic disease caused by an infection by human immunodeficiency virus (HIV-1, HIV-2), a retrovirus that causes immune system failure and debilitation and is often accompanied by infections such as tuberculosis).

The term "HIV-related neuropathy" refers to a neuropathy in a mammal infected with HIV were the neuropathy is caused by infections such as CMV or other viruses of the herpes family. Neuropathy is the name given to a group of disorders whose symptoms may range from a tingling sensation or numbness in the toes and fingers to paralysis. Neuropathy might more accurately be called "neuropathies" because there are several types and can be painful.

The term "ocular damage" refers to any damage to the eyes or in relation to the eyes.

The term "retinopathy" refers to any pathological disorder of the retina.

The term "cognitive disorder" refers to any cognitive dysfunction, for example, disturbance of memory (e.g., amnesia) or learning.

The term "neuronal injury associated with HIV infection" refers to damage/injury of nerve cells caused either directly or indirectly by infection with HIV.

The term "dysfunction in cognition, movement and sensation" refers to abnormal or impaired functioning in cognition (mental process of knowing, including aspects such as awareness, perception, reasoning, and judgment), movement or sensation.

Any of the above diseases, disorders, or conditions can be treated by administering a compound or composition that includes a compound described herein to treat the disease, disorder, or condition by inhibiting matrix a metalloproteinase.

The following Examples illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Preparation of MMP Inhibitors and Prodrugs

The p-aminophenoxybenzene scaffold was assembled by the methodology developed by Ikejiri et al. (*J. Biol. Chem.* 2005, 280, 33992-34002). This methodology includes the coupling of 1-fluoro-4-nitrobenzene (1) and 4-(allylthio)phenol (2) under basic condition, followed by reduction of the nitro group to amine over elemental zinc in acetic acid. The resulting amine 3 was treated with di-tert-butyl dicarbonate to give the Boc protected compound 4. The Boc group was chosen as the amine protecting group because the sulfonylmethylthiirane is relatively stable under acidic condition that is used for the removal of Boc at the end of the synthesis (see transformation of 5 to 6). The rest of the transformations, including oxidation to sulfone, epoxide formation using m-chloroperbenzoic acid, and thiirane conversion using thiourea, were performed by the methodology developed by the Mobashery group earlier (*Org. Lett.* 2005, 7, 4463-4465; *J. Org. Chem.* 2004, 69, 3572-3573). Removal of the Boc group in compound 5 was carried out in the presence of 4 N HCl in 1,4-dioxane at room temperature for 24 hours to yield compound 6 as the HCl salt in 82%.

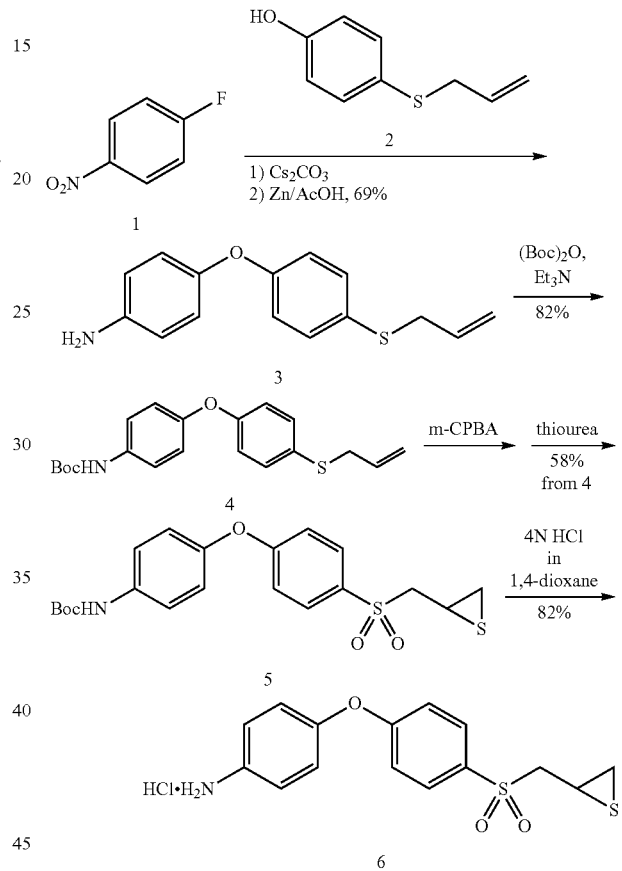

Scheme 1. Synthesis of Compound 6.

Syntheses of amino acid conjugates of benzamine (6) and phenol (7) as prodrugs of gelatinase inhibitors are outlined in Scheme 2. Compound 7, prepared according to the literature (*Chem. Biol. & Drug Des.* 2009, 73, 189-202), was acylated with Boc-protected N-hydroxysuccinimide esters of amino acids (Gly, L-Lys, L-Glu, L-Arg, and L-Arg-L-Arg) in the presence of 4-(dimethylamino)pyridine (DMAP) to give the ester 8. The Boc group in compound 8, in turn, was readily removed by treatment with 4 N HCl in 1,4-dioxane to result in the ester prodrug 9. The acid treatment for removal of the Boc group in the presence of thiirane works well, as described in Scheme 1 for the synthesis of compound 6.

When the compound 6 was subjected to the same acylation conditions, the desired amide bond was not formed, instead, it gave only recovery of the two starting materials. Boc-protected amino acid was activated to mixed anhydride by treatment of isobutyl chloroformate in the presence of N-methylmorpholine, which was allowed to react with compound 6 to give the desired amide linkage. The removal of Boc group in compound 10 was carried out by acid treatment resulting in the amide prodrug 11.

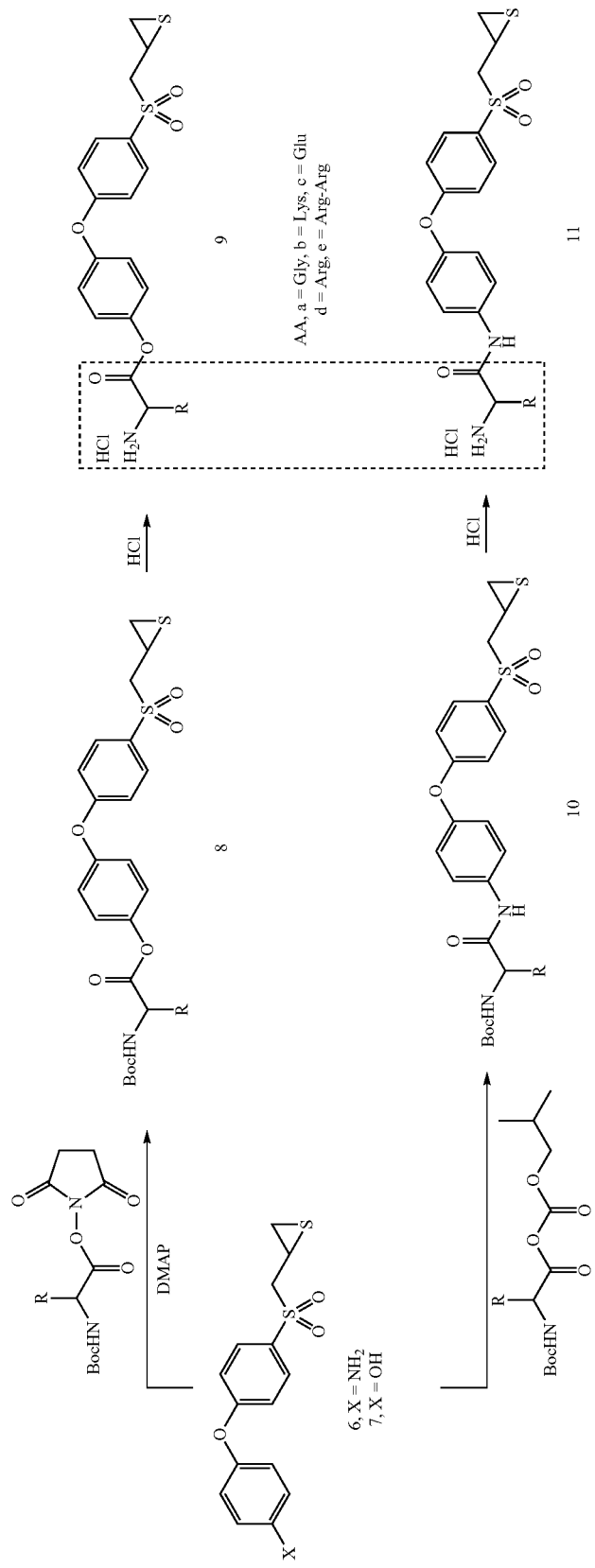
Scheme 2. Preparation of Prodrugs 9 and 11.

When compounds 6 and 7 were treated with p-nitrophenyl carbonate presence of DAMP, the desired prodrugs 13 and 14 were accessed.
Scheme 3. Prepartion of Prodrugs 13 and 14.
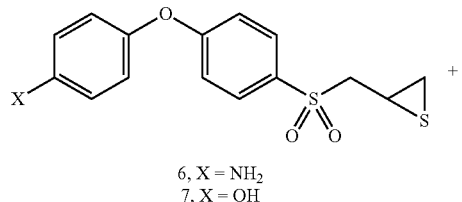
Scheme 4. Synthesis of Compound 22.
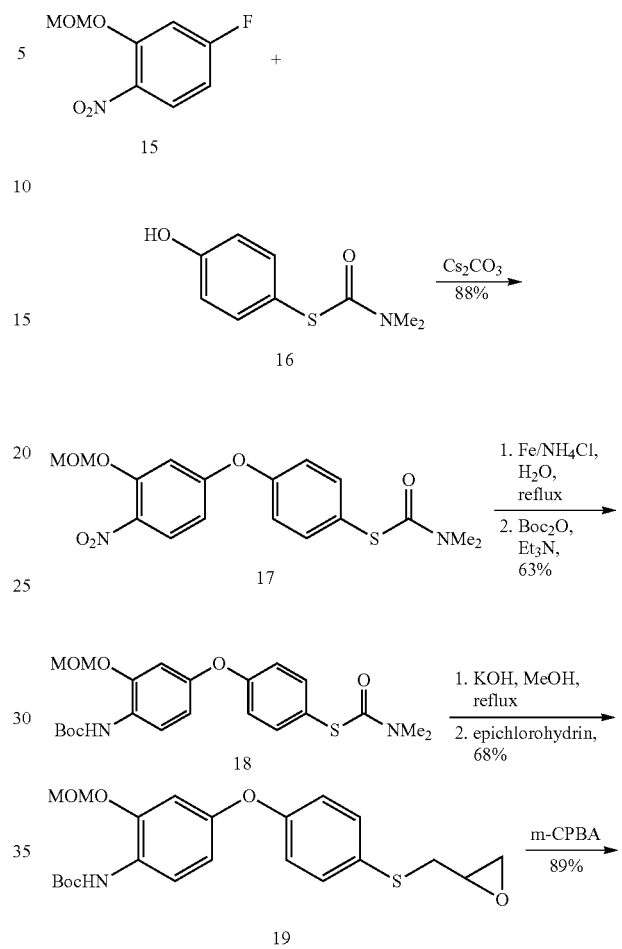
TABLE 1
Various Specific Prodrugs.
| X | Compound No | Compound No |
|---|---|---|
| Gly | 9a | 11a |
| Lys | 9b | 11b |
| Glu | 9c | 11c |
| Arg | 9d | 11d |
| Arg-Arg | 9e | 11e |
| dioxolone* | 13 | 14 |
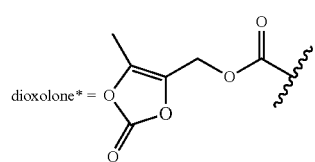 [SMILES: *C(=O)OCc1oc(=O)oc1C]

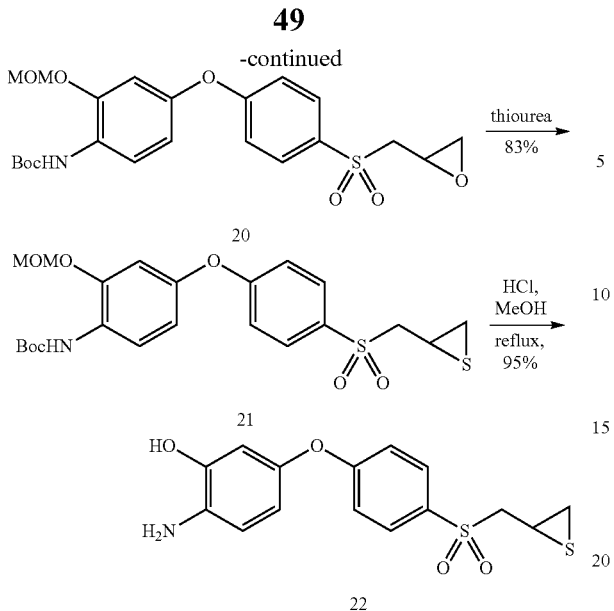

Experimental Procedures t-Butyl[4-(4-allylthiophenoxyl)phenyl]carbamate (4)

Compound 3 (10.3 g, 40.0 mmol), which was prepared by a literature method (*J. Biol. Chem.* 2005, 280, 33992-34002), was dissolved in a mixture of MeOH and triethylamine (7:1, 80 mL) and di-t-butyldicarbonate (17.5 g, 80 mmol) was added. The resulting solution was stirred for 2 h at 60° C. and concentrated under reduced pressure. The crude material was purified by column chromatography on silica gel to give the title compound (11.7 g, 82%). $^1$H NMR (600 MHz, CDCl$_3$) δ 1.53 (s, 9H), 3.48 (d, J=6.7 Hz, 2H), 4.96-5.09 (m, 2H), 5.86 (m, J=16.7, 10.3 Hz, 1H), 6.47 (br. s, 1H), 6.89 (d, J=8.8 Hz, 2H), 6.96 (d, J=8.8 Hz, 2H), 7.24-7.39 (m, 4H); $^{13}$C NMR (151 MHz, CDCl$_3$) δ 28.5, 38.9, 80.7, 117.7, 118.6, 120.3, 120.5, 128.9, 133.3, 134.0, 134.5, 152.2, 153.1, 157.4; HRMS-FAB (m/z): [M]$^+$, calcd for C$_{20}$H$_{23}$NO$_3$S, 357.1399. found, 357.1402.

t-Butyl[4-(4-(thiiran-2-yl)methylsulfonylphenoxy)phenyl]carbamate (5)

To a solution of compound 4 (10.0 g, 28.0 mmol) in CH$_2$Cl$_2$ (100 mL) was added a solution of m-chloroperoxybenzoic acid (31.2 g, 140 mmol, 77%) in an ice-water bath. After 48 h, the suspension was filtered and the filtrate was diluted with EtOAc and washed with 10% aqueous sodium thiosulfate, followed by washes with saturated sodium bicarbonate and brine. The organic layer was dried over MgSO$_4$ and was concentrated. The product was purified by silica gel chromatography to yield the oxirane (7.4 g, 81%) with recovery of some of the allylsulfone derivative (2.1 g, 19%). $^1$H NMR (600 MHz, CDCl$_3$) δ 1.50 (s, 9H), 2.45 (dd, J=5.0, 1.2 Hz, 1H), 2.79 (dd, J=4.4, 2.6 Hz, 1H), 3.24-3.34 (m, 3H), 6.85 (s, 1H), 6.99 (d, J=8.8 Hz, 2H), 7.02 (d, 2H), 7.42 (d, J=8.2 Hz, 2H), 7.84 (d, J=8.8 Hz, 2H); $^{13}$C NMR (151 MHz, CDCl$_3$) δ 28.4, 46.0, 46.0, 59.7, 117.2, 120.5, 121.3, 130.6, 132.2, 136.0, 149.8, 153.0, 163.4; HRMS-FAB (m/z): [M]$^+$, calcd for C$_{20}$H$_{23}$NO$_6$S, 405.1246. found, 405.1230.

Thiourea (2.4 g, 31.5 mmol) was added to a solution of oxirane (6.0 g, 14.8 mmol), obtained above, in a 1:1 mixture of methanol and CH$_2$Cl$_2$ (50 mL). The reaction mixture was stirred at room temperature for 24 h. The solvent was removed under reduced pressure. The residue was partitioned between CH$_2$Cl$_2$ and water, the organic layer was washed with brine and water, dried (MgSO$_4$) and the suspension was filtered. Evaporation of solvent gave the crude product, which was purified by column chromatography on silica gel to give thiirane 5 (4.4 g, 72%). $^1$H NMR (600 MHz, CDCl$_3$) δ 1.53 (s, 9H), 2.16 (dd, J=5.1, 1.6 Hz, 1H), 2.54 (dd, J=6.2, 1.2 Hz, 1H), 3.06 (dq, J=7.6, 5.7 Hz, 1H), 3.17 (dd, J=14.1, 7.9 Hz, 1H), 3.53 (dd, J=14.1, 5.6 Hz, 1H), 6.61 (br. s, 1H), 7.06 (d, J=8.8 Hz, 2H), 7.03 (d, J=8.8 Hz, 2H), 7.44 (d, J=8.5 Hz, 2H), 7.84 (d, J=8.8 Hz, 2H); $^{13}$C NMR (151 MHz, CDCl$_3$) δ 24.5, 26.3, 28.5, 62.8, 81.0, 117.4, 120.6, 121.4, 130.9, 131.8, 136.0, 150.0, 153.0, 163.6; HRMS-FAB (m/z): [M]$^+$, calcd for C$_{20}$H$_{23}$NO$_5$S$_2$, 421.1018. found, 421.1009.

4-[4-((Thiiran-2-yl)methylsulfonyl)phenoxy]benzamine.HCl salt

The thiirane (4.0 g, 9.5 mmol) was dissolved in a 1:1 mixture of CH$_2$Cl$_2$ and ethyl acetate (40 mL) and HCl (10 mL, 4 N in dioxane) was added. The reaction mixture was stirred for 24 h and concentrated under reduced pressure. The resulting crude compound was triturated with diethyl ether and the product was obtained by filtration (2.8 g, 82%). $^1$H NMR (500 MHz, D$_2$O) δ 2.03 (d, J=4.8 Hz, 1H), 2.42 (d, J=6.4 Hz, 1H), 2.94 (m, J=6.4, 6.4 Hz, 1H), 3.42 (dd, J=14.4, 6.4 Hz, 1H), 3.61 (dd, J=14.4, 6.4 Hz, 1H), 7.11 (d, J=8.0 Hz, 2H), 7.16 (d, J=8.0 Hz, 2H), 7.35 (d, J=8.0 Hz, 2H), 7.80 (d, J=8.0 Hz, 2H); $^{13}$C NMR (126 MHz, D$_2$O) δ 23.5, 26.0, 61.4, 118.6, 121.9, 125.2, 126.8, 130.8, 131.1, 155.2, 162.5; HRMS-FAB (m/z): [M+H]$^+$, calcd for C$_{15}$H$_{16}$NO$_3$S$_2$, 322.0572. found, 322.0569.

Syntheses of Ester Prodrugs (9)

Synthesis of the lysine prodrug (9b) is provided here as a representative example.

To a solution of 7 (0.20 g, 0.62 mmol) (prepared according to the method of Stella and Nti-Addae; *Adv. Drug Deliv. Rev.* 2007, 59, 677-94) in CH$_2$Cl$_2$ (5 mL) was added N$_\alpha$,N$_\epsilon$-di-Boc-L-lysine hydroxysuccinimide ester (0.41 g, 0.93 mmol) at room temperature. 4-Dimethylamino-pyridine (76 mg, 0.62 mmol) was added and the reaction mixture was stirred for 3 h at room temperature. After concentrating under reduced pressure, the crude product was purified by column chromatography on silica gel to give the desired product (8b, 0.30 g, 74%). The ester (0.30 g, 0.46 mmol) was dissolved in CH$_2$Cl$_2$ and ethyl acetate (1:1, 4 mL) and HCl (2 mL, 4 N in dioxane) was added. The reaction mixture was stirred for 24 h and concentrated under reduced pressure. The resulting crude compound was triturated with diethyl ether and the product (9b) was obtained by filtration (0.18 g, 75%).

Syntheses of Amide Prodrugs (11)

Synthesis of the lysine prodrug (11b) is provided as a representative example.

i-Butylchloroformate (83 μL, 0.53 mmol) was added to a mixture of N$_\alpha$,N$_\epsilon$-di-Boc-L-lysine dicyclohexylamine salt (0.28 g, 0.64 mmol) and N-methylmorpholine (140 μL, 1.3 mmol) in THF (4 mL) at −15° C. After stirring for 0.5 h at the same temperature, the suspension of 6 (0.19 g, 0.53 mmol) and N-methylmorpholine (58 μL, 0.53 mmol) in THF (2 mL) was added to the reaction mixture. Stirring was continued for 1 h, while temperature was gradually increased to room temperature. The reaction mixture was diluted with $CH_2Cl_2$/water and layers were separated. The aqueous layer was extracted and the combined organic layers were dried ($MgSO_4$) and evaporated. The crude material was purified by column chromatography on silica gel to afford the desired product (10b, 0.21 g, 64%). Amide (0.20 g, 0.30 mmol) was dissolved in $CH_2Cl_2$ and ethyl acetate (1:1, 3 mL) and HCl (2 mL, 4 N in dioxane) was added. The reaction mixture was stirred for 24 h and concentrated under reduced pressure. The resulting crude compound was triturated with diethyl ether and the product (11b) was obtained by filtration (0.11 g, 71%).

Spectral data of Gly ester prodrug compound 8a. $^1$H NMR (500 MHz, $CDCl_3$) δ 1.48 (s, 9H), 2.17 (dd, J=5.0, 1.8 Hz, 1H), 2.55 (dd, J=6.2, 1.8 Hz, 1H), 3.04-3.10 (m, 1H), 3.20 (dd, J=14.4, 7.8 Hz, 1H), 3.52 (dd, J=14.2, 5.6 Hz, 1H), 4.19 (d, J=5.8 Hz, 2H), 7.11 (d, J=9.0 Hz, 2H), 7.12 (d, J=8.8 Hz, 2H), 7.18 (d, J=9.0 Hz, 2H), 7.88 (d, J=9.0 Hz, 2H); $^{13}$C NMR (126 MHz, $CDCl_3$) δ 24.4, 26.2, 28.5, 42.7, 62.7, 80.5, 117.9, 121.5, 123.3, 131.0, 132.4, 147.3, 152.6, 162.8, 169.3; HRMS-ESI (m/z): [M+H]$^+$, calcd for $C_{22}H_{26}N_2O_6S_2$, 480.1145. found, 480.1145.

Compound 9a. $^1$H NMR (500 MHz, $D_2O$) δ 2.17 (dd, J=5.2, 1.2 Hz, 1H), 2.56 (d, J=6.2 Hz, 1H), 3.09 (quin, J=6.2 Hz, 1H), 3.57 (dd, J=14.6, 7.2 Hz, 1H), 3.74 (dd, J=14.6, 6.4 Hz, 1H), 4.25 (s, 2H), 7.21-7.35 (m, 6H), 7.93 (d, J=8.8 Hz, 2H); HRMS-ESI (m/z): [M+H]$^+$, calcd for $C_{17}H_{18}NO_5S_2$, 380.0621. found, 380.0597.

Spectral data of Lys ester prodrug compound 8b. $^1$H NMR (500 MHz, $CDCl_3$) δ 1.45 (s, 9H), 1.47 (s, 9H), 1.52 (m, 2H), 1.56 (m, 4H), 1.85 (m, 1H), 1.99 (m, 1H), 2.17 (dd, J=5.2, 1.8 Hz, 1H), 2.55 (dd, J=6.2, 1.8 Hz, 1H), 3.07 (m, 1H), 3.17 (m, 2H), 3.19 (dd, J=14.2, 7.8 Hz, 1H), 3.53 (dd, J=14.2, 5.6 Hz, 1H), 4.49 (m, 1H), 4.61 (m, 1H), 5.23 (d, J=7.4 Hz, 1H), 7.10 (d, J=9.0 Hz, 1H), 7.11 (d, J=8.8 Hz, 2H), 7.17 (d, J=9.0 Hz, 1H); $^{13}$C NMR (126 MHz, $CDCl_3$) δ 22.7, 24.4, 26.3, 28.5, 28.6, 29.9, 32.1, 40.1, 53.8, 62.8, 79.5, 80.3, 81.3, 117.9, 121.6, 123.4, 131.0, 132.4, 147.6, 152.6, 162.9, 171.8; HRMS-ESI (m/z): [M+H]$^+$, calcd for $C_{31}H_{43}N_2O_9S_2$, 651.2404. found, 651.2414.

Compound 9b. $^1$H NMR (500 MHz, 10% $CDCl_3$ in $CD_3OD$) δ 1.62-1.84 (m, 4H), 2.05-2.26 (m, 2H), 2.14 (dd, J=5.0, 1.4 Hz, 1H), 2.52 (dd, J=6.3, 1.1 Hz, 1H), 3.01 (t, J=7.6 Hz, 2H), 3.06 (m, 1H), 3.46 (dd, J=14.6, 7.0 Hz, 1H), 3.54 (t, J=6.6 Hz, 1H), 4.40 (t, J=6.5 Hz, 1H), 7.19 (d, J=9.0 Hz, 2H), 7.23 (d, J=9.0 Hz, 2H), 7.32 (d, J=9.2 Hz, 2H), 7.94 (d, J=9.0 Hz, 2H); HRMS-ESI (m/z): [M+H]$^+$, calcd for $C_{21}H_{27}N_2O_5S_2$, 451.1356. found, 541.1298.

Spectral data of Glu ester prodrug compound 8c. $^1$H NMR (500 MHz, $CDCl_3$) δ 1.45 (s, 18H), 2.09 (m, 1H), 2.15 (dd, J=5.2, 1.8 Hz, 1H), 2.29 (m, 1H), 2.43 (q, J=7.4 Hz, 2H), 2.52 (dd, J=6.2, 1.8 Hz, 1H), 3.05 (m, 1H), 3.18 (dd, J=14.4, 7.8 Hz, 1H), 3.51 (dd, J=14.4, 5.8 Hz, 1H), 4.52 (m, 1H), 5.26 (d, J=8.2 Hz, 1H), 7.08 (d, J=9.0 Hz, 2H), 7.09 (d, J=9.0 Hz, 2H), 7.17 (d, J=9.2 Hz, 2H), 7.86 (d, J=9.0 Hz, 2H); $^{13}$C NMR (126 MHz, $CDCl_3$) δ 24.4, 26.2, 27.3, 28.2, 28.4, 31.7, 53.5, 62.7, 80.4, 81.1, 117.9, 121.4, 123.3, 130.9, 132.3, 147.5, 152.5, 155.6, 162.8, 171.3, 172.1; HRMS-ESI (m/z): [M+H]$^+$, calcd for $C_{29}H_{38}NO_9S_2$, 608.1982. found, 608.1981.

Compound 9c. $^1$H NMR (500 MHz, 10% $CDCl_3$ in $CD_3OD$) δ 2.14 (dd, J=5.1, 1.3 Hz, 1H), 2.37 (m, 2H), 2.52 (dd, J=6.2, 1.0 Hz, 1H), 2.68 (td, J=7.1, 1.6 Hz, 2H), 3.05 (quin, J=6.2 Hz, 1H), 3.44 (dd, J=14.4, 7.0 Hz, 1H), 3.54 (dd, J=14.4, 6.4 Hz, 1H), 4.43 (t, J=6.8 Hz, 1H), 7.19 (d, J=8.8 Hz, 2H), 7.22 (d, J=9.2 Hz, 2H), 7.32 (d, J=9.0 Hz, 2H), 7.93 (d, J=9.0 Hz, 2H); HRMS-ESI (m/z): [M+H]$^+$, calcd for $C_{20}H_{22}NO_7S_2$, 452.0832. found, 452.0769.

Spectral data of Arg ester prodrug compound 8d. $^1$H NMR (500 MHz, $CDCl_3$) δ 1.46 (s, 9H), 1.50 (s, 9H), 1.77 (m, 1H), 1.94 (m, 1H), 2.13 (dd, J=5.0, 1.6 Hz, 1H), 2.51 (dd, J=6.2, 1.6 Hz, 1H), 3.03 (m, 1H), 3.17 (dd, J=14.2, 7.8 Hz, 1H), 3.49 (dd, J=14.2, 5.6 Hz, 1H), 3.84 (m, 1H), 3.96 (m, 1H), 4.50 (m, 1H), 5.83 (d, J=8.2 Hz, 1H), 7.07 (d, J=9.0 Hz, 2H), 7.08 (d, J=8.8 Hz, 2H), 7.14 (d, J=9.0 Hz, 1H), 7.85 (d, J=9.0 Hz, 2H); $^{13}$C NMR (126 MHz, $CDCl_3$) δ 24.3, 26.2, 28.1, 28.3, 28.5, 44.1, 53.5, 60.5, 62.7, 84.1, 117.8, 121.4, 123.4, 130.9, 132.3, 147.7, 152.4, 155.0, 155.6, 160.6, 162.8, 163.6, 171.2; HRMS-ESI (m/z): [M+H]$^+$, calcd for $C_{36}H_{51}N_4O_{11}S_2$, 779.2990. found, 779.3001.

Compound 9d. $^1$H NMR (500 MHz, 10% $CDCl_3$ in $CD_3OD$) δ 1.78-2.26 (m, 4H), 2.14 (dd, J=5.1, 1.3 Hz, 1H), 2.52 (dd, J=6.2, 0.8 Hz, 1H), 3.04 (quin, J=6.2 Hz, 1H), 3.27 (m, 2H), 3.43 (dd, J=14.4, 7.0 Hz, 1H), 3.52 (dd, J=14.8, 6.6 Hz, 1H), 4.39 (t, J=6.5 Hz, 1H), 7.17 (d, J=9.0 Hz, 1H), 7.21 (d, J=9.0 Hz, 1H), 7.30 (d, J=9.0 Hz, 2H), 7.92 (d, J=8.8 Hz, 2H); HRMS-ESI (m/z): [M+H]$^+$, calcd for $C_{21}H_{27}N_4O_5S_2$, 479.1417. found, 479.1423.

Spectral data of Arg-Arg ester prodrug compound 8e. $^1$H NMR (500 MHz, $CDCl_3$) δ 1.39-1.53 (m, 45H), 1.54-2.11 (m, 8H), 2.16 (dd, J=5.2, 1.4 Hz, 1H), 2.54 (d, J=5.2 Hz, 1H), 3.06 (m, 1H), 3.19 (dd, J=14.2, 7.8 Hz, 1H), 3.47 (dd, J=12.8, 7.0 Hz, 2H), 3.52 (dd, J=14.4, 5.6 Hz, 1H), 3.74-3.95 (m, 2H), 4.32 (dd, J=14.8, 6.4 Hz, 1H), 4.77 (m, 1H), 5.92 (d, J=7.8 Hz, 1H), 7.07-7.12 (m, 4H), 7.16 (d, J=9.0 Hz, 2H), 7.33 (d, J=7.6 Hz, 1H), 7.87 (d, J=8.8 Hz, 2H), 8.38 (t, J=4.9 Hz, 1H), 9.30 (br. s, 2H), 11.50 (s, 1H); $^{13}$C NMR (126 MHz, $CDCl_3$) δ 24.4, 24.9, 25.6, 26.2, 28.2, 28.2, 28.5, 28.6, 29.3, 40.4, 44.1, 52.5, 54.3, 62.8, 79.5, 80.2, 83.4, 83.5, 84.2, 117.9, 121.5, 121.5, 123.4, 130.8, 131.0, 132.3, 147.5, 152.5, 153.4, 155.0, 156.4, 160.8, 160.9, 162.9, 163.7, 170.6, 172.7; HRMS-ESI (m/z): [M+H]$^+$, calcd for $C_{52}H_{79}N_8O_{16}S_2$, 1135.5050. found, 1135.5039.

Compound 9e. $^1$H NMR (500 MHz, 10% $CDCl_3$ in $CD_3OD$) δ 1.71-2.23 (m, 8H), 2.16 (dd, J=5.0, 1.2 Hz, 1H), 2.54 (dd, J=6.2, 0.8 Hz, 1H), 3.03-3.10 (m, 1H), 3.23-3.32 (m, 4H), 3.47 (dd, J=14.4, 7.0 Hz, 1H), 3.54 (dd, J=14.2, 6.4 Hz, 1H), 4.16 (t, J=6.4 Hz, 1H), 4.72 (dd, J=9.1, 4.5 Hz, 1H), 7.15-7.23 (m, 4H), 7.25 (d, J=9.0 Hz, 2H), 7.94 (d, J=8.8 Hz, 2H); HRMS-ESI (m/z): [M+H]$^+$, calcd for $C_{27}H_{39}N_8O_6S_2$, 635.2428. found, 635.2449.

Spectral data of Gly amide prodrug compound 10a. $^1$H NMR (500 MHz, $CDCl_3$) δ 1.37 (s, 9H), 2.05 (dd, J=5.2, 1.8 Hz, 1H), 2.44 (dd, J=6.2, 1.8 Hz, 1H), 2.94 (m, 1H), 3.14 (dd, J=14.4, 7.6 Hz, 1H), 3.41 (dd, J=14.4, 6.0 Hz, 1H), 3.80 (d, J=5.2 Hz, 2H), 3.82 (s, 1H), 6.96 (d, J=15.2 Hz, 2H), 6.98 (d, J=15.4 Hz, 2H), 7.52 (d, J=8.8 Hz, 2H), 7.75 (d, J=9.0 Hz, 2H); $^{13}$C NMR (126 MHz, $CDCl_3$) δ 24.0, 25.9, 28.2, 44.2, 62.5, 80.4, 117.4, 121.0, 121.8, 130.7, 131.4, 150.7, 163.3, 168.3, 172.9; HRMS-ESI (m/z): [M+Na]$^+$, calcd for $C_{22}H_{26}N_2O_6S_2Na$, 501.1124. found, 501.1112.

Compound 11a. $^1$H NMR (500 MHz, 10% $CDCl_3$ in $CD_3OD$) δ 2.14 (dd, J=5.2, 1.6 Hz, 1H), 2.51 (dd, J=6.3, 1.5 Hz, 1H), 3.04 (m, J=7.0, 5.2 Hz, 1H), 3.42 (dd, J=14.4, 7.0 Hz, 1H), 3.53 (dd, J=14.4, 6.4 Hz, 1H), 4.14 (s, 2H), 7.17 (d, J=9.0, 2.0, 1.8 Hz, 1H), 7.20 (d, J=9.2 Hz, 2H), 7.29 (d, J=9.2 Hz, 2H), 7.92 (d, J=9.2 Hz, 1H); HRMS-ESI (m/z): [M+H]$^+$, calcd for $C_{17}H_{19}N_2O_4S_2$, 379.0781. found, 379.0805.

Spectral data of Lys amide prodrug compound 10b. $^1$H NMR (500 MHz, $CDCl_3$) δ 1.41 (s, 9H), 1.43 (s, 9H), 2.02 (s, 3H), 2.13 (dd, J=5.0, 1.6 Hz, 1H), 2.50 (dd, J=6.2, 1.6 Hz, 1H), 3.02 (m, 1H), 3.09 (m, 2H), 3.16 (dd, J=14.4, 7.8 Hz, 1H), 3.50 (dd, J=14.4, 5.8 Hz, 1H), 4.28 (m, 1H), 4.75 (m, 1H), 5.53 (d, J=7.4 Hz, 1H), 6.93 (d, J=8.4 Hz, 2H), 7.00 (d, J=8.6 Hz, 2H), 7.55 (d, J=8.8 Hz, 2H), 7.82 (d, J=9.0 Hz, 2H);

$^{13}$C NMR (126 MHz, CDCl$_3$) δ 24.4, 26.2, 28.5, 28.6, 29.8, 31.9, 39.8, 55.3, 62.7, 79.3, 80.5, 117.4, 121.1, 121.7, 130.8, 131.8, 135.6, 150.5, 156.4, 156.6, 163.3, 171.2; HRMS-ESI (m/z): [M+Na]$^+$, calcd for C$_{31}$H$_{43}$N$_3$O$_8$S$_2$Na, 672.2384. found, 672.2393.

Compound 11b. $^1$H NMR (500 MHz, 10% CDCl$_3$ in CD$_3$OD) δ 1.59-1.86 (m, 4H), 2.06-2.25 (m, 2H), 2.14 (dd, J=5.2, 1.4 Hz, 1H), 2.52 (dd, J=6.4, 1.4 Hz, 1H), 3.00 (t, J=7.6 Hz, 2H), 3.05 (m, 1H), 3.45 (dd, J=14.4, 6.8 Hz, 1H), 3.53 (dd, J=14.6, 6.6 Hz, 1H), 4.39 (t, J=6.5 Hz, 1H), 7.18 (d, J=8.8 Hz, 2H), 7.22 (d, J=9.2 Hz, 2H), 7.32 (d, J=9.0 Hz, 2H), 7.93 (d, J=9.0 Hz, 2H); HRMS-ESI (m/z): [M+H]$^+$, calcd for C$_{21}$H$_{28}$N$_3$O$_4$S$_2$, 450.1516. found, 450.1485.

Spectral data of Glu amide prodrug compound 10c. $^1$H NMR (500 MHz, CDCl$_3$) δ 1.47 (s, 9H), 1.49 (s, 9H), 2.00 (m, 1H), 2.17 (dd, J=5.2, 1.8 Hz, 1H), 2.41 (m, 1H), 2.56 (m, 2H), 3.07 (m, 1H), 3.18 (dd, J=14.3, 7.9 Hz, 1H), 3.54 (dd, J=14.1, 5.5 Hz, 1H), 4.27 (m, 1H), 7.07 (d, J=8.6 Hz, 2H), 7.08 (d, J=9.0 Hz, 2H), 7.61 (d, J=9.0 Hz, 1H), 7.86 (d, J=9.0 Hz, 1H); $^{13}$C NMR (126 MHz, CDCl$_3$) δ 24.5, 26.3, 28.2, 28.5, 37.1, 51.5, 62.8, 82.3, 117.6, 121.3, 121.9, 130.9, 131.9, 135.2, 151.0, 163.3, 169.3, 171.7; HRMS-ESI (m/z): [M+Na]$^+$, calcd for C$_{29}$H$_{38}$N$_2$O$_8$S$_2$Na, 629.1962. found, 629.1969.

Compound 11c. $^1$H NMR (500 MHz, 10% CDCl$_3$ in CD$_3$OD) δ 2.32 (m, 1H), 2.42 (m, 1H), 2.51 (dd, J=6.2, 1.4 Hz, 1H), 2.68 (dt, J=7.2, 6.8, 2.0 Hz, 2H), 3.04 (m, 1H), 3.44 (dd, J=14.4, 7.0 Hz, 1H), 3.53 (dd, J=14.4, 6.4 Hz, 1H), 4.43 (t, J=6.8 Hz, 1H), 4.87 (s, 10H), 7.19 (d, J=9.2 Hz, 2H), 7.22 (d, J=9.2 Hz, 2H), 7.32 (d, J=9.2 Hz, 2H); HRMS-ESI (m/z): [M+H]$^+$, calcd for C$_{20}$H$_{23}$N$_2$O$_6$S$_2$, 451.0992. found, 451.1004.

Spectral data of Arg amide prodrug compound 10d. $^1$H NMR (500 MHz, CDCl$_3$) δ 1.38 (s, 9H), 1.48 (s, 9H), 1.53 (s, 9H), 1.59-1.96 (m, 4H), 2.16 (dd, J=5.2, 1.8 Hz, 1H), 2.54 (dd, J=6.2, 1.6 Hz, 1H), 3.06 (m, 1H), 3.17 (dd, J=14.2, 8.0 Hz, 1H), 3.53 (dd, J=14.2, 5.6 Hz, 1H), 3.72 (m, 1H), 4.12 (s, 1H), 4.55 (m, 1H), 5.99 (d, J=8.2 Hz, 1H), 7.05 (d, J=9.0 Hz, 2H), 7.07 (d, J=8.8 Hz, 2H), 7.53 (d, J=8.6 Hz, 2H), 7.85 (d, J=9.0 Hz, 2H), 9.13 (br. s, 1H); $^{13}$C NMR (126 MHz, CDCl$_3$) δ 24.5, 24.7, 26.3, 28.2, 28.6, 29.3, 44.1, 54.0, 62.8, 84.6, 117.6, 121.2, 123.4, 130.9, 132.0, 135.1, 151.3, 155.0, 161.3, 163.2, 163.4, 171.1; HRMS-ESI (m/z): [M+H]$^+$, calcd for C$_{36}$H$_{52}$N$_5$O$_{10}$S$_2$, 778.3150. found, 778.3154.

Compound 11d. $^1$H NMR (500 MHz, 10% CDCl$_3$ in CD$_3$OD) δ 1.71-2.11 (m, 4H), 2.16 (d, J=5.2 Hz, 1H), 2.54 (dd, J=6.2, 1.2 Hz, 1H), 3.06 (quin, J=6.2 Hz, 1H), 3.29 (m, 1H), 3.45 (m, 2H), 3.54 (dd, J=14.6, 6.4 Hz, 1H), 4.14 (m, 1H), 7.15 (d, J=9.0 Hz, 2H), 7.15 (d, J=9.0 Hz, 2H), 7.77 (d, J=9.0 Hz, 2H), 7.92 (d, J=8.8 Hz, 2H); HRMS-ESI (m/z): [M+H]$^+$, calcd for C$_{21}$H$_{28}$N$_5$O$_4$S$_2$, 478.1577. found, 478.1580.

Spectral data of Arg-Arg amide prodrug compound 10e. $^1$H NMR (500 MHz, CDCl$_3$) δ 1.40-1.54 (5×s, 45H), 1.46-1.90 (m, 8H), 2.16 (dd, J=5.2, 1.8 Hz, 1H), 2.53 (dd, J=6.2, 1.4 Hz, 1H), 3.05 (m, 1H), 3.16 (dd, J=14.2, 7.8 Hz, 1H), 3.39 (m, 1H), 3.53 (dd, J=14.2, 5.6 Hz, 1H), 3.55 (m, 2H), 3.82 (t, J=6.8 Hz, 2H), 4.28 (dd, J=13.8, 6.4 Hz, 1H), 4.59 (q, J=7.4 Hz, 1H), 6.10 (d, J=7.4 Hz, 1H), 7.03 (d, J=9.0 Hz, 2H), 7.05 (d, J=8.8 Hz, 2H), 7.22 (d, J=6.4 Hz, 1H), 7.61 (d, J=8.4 Hz, 2H), 7.84 (d, J=9.0 Hz, 2H), 8.41 (t, J=5.6 Hz, 1H), 8.84 (s, 1H), 9.26 (br. s, 1H), 9.35 (br. s, 1H), 11.47 (s, 1H); $^{13}$C NMR (126 MHz, CDCl$_3$) δ 22.8, 24.5, 25.4, 26.1, 26.2, 28.2, 28.2, 28.4, 28.4, 28.6, 29.2, 31.8, 34.8, 40.1, 44.1, 53.8, 55.0, 62.8, 79.6, 80.6, 83.4, 84.3, 117.5, 121.2, 122.5, 130.9, 131.8, 135.4, 150.9, 153.4, 154.9, 156.6, 160.8, 163.4, 163.4, 163.5, 169.6; HRMS-ESI (m/z): [M+H]$^+$, calcd for C$_{52}$H$_{80}$N$_9$O$_{15}$S$_2$, 1134.5210. found, 1134.5215.

Compound 11e. $^1$H NMR (500 MHz, 10% CDCl$_3$ in CD$_3$OD) δ 1.68-2.05 (m, 8H), 2.13 (dd, J=5.1, 1.3 Hz, 1H), 2.51 (dd, J=6.2, 1.0 Hz, 1H), 3.17 (m, 1H), 3.22-3.28 (m, 4H), 3.42 (dd, J=14.6, 7.0 Hz, 1H), 3.50 (dd, J=14.0, 7.0 Hz, 1H), 4.10 (t, J=6.3 Hz, 1H), 4.52 (dd, J=8.7, 5.1 Hz, 1H), 7.10 (t, J=8.9 Hz, 4H), 7.66 (d, J=9.0 Hz, 2H), 7.89 (d, J=9.0 Hz, 2H); HRMS-ESI (m/z): [M+H]$^+$, calcd for C$_{27}$H$_{40}$N$_9$O$_5$S$_2$, 634.2588. found, 634.2585.

Syntheses of Dioxolone Prodrugs.

A solution of compound 7 (0.10 g, 0.31 mmol) and 5-methyl-2-oxo-1,3-dioxol-4-en-4-yl)methyl p-nitrophenyl carbonate (0.10 g, 0.34 mmol) in CH$_2$Cl$_2$ (2 mL) was stirred at room temperature for 2 h. The reaction mixture was concentrated and after column chromatography on silica gel, the desired product 13 was obtained (0.11 g, 71%). $^1$H NMR (500 MHz, CDCl$_3$) δ 2.15 (dd, J=5.2, 1.8 Hz, 1H), 2.21 (s, 6H), 2.52 (dd, J=6.2, 1.4 Hz, 1H), 3.04 (m, J=7.0, 6.0 Hz, 1H), 3.20 (dd, J=14.3, 7.7 Hz, 1H), 3.49 (dd, J=14.3, 5.9 Hz, 1H), 5.01 (s, 2H), 7.11 (d, J=9.2 Hz, 2H), 7.10 (d, J=9.0 Hz, 2H), 7.24 (d, J=9.2 Hz, 2H), 7.87 (d, J=9.0 Hz, 2H); $^{13}$C NMR (126 MHz, CDCl$_3$) δ 9.6, 24.3, 26.2, 57.9, 62.7, 77.4, 118.0, 121.5, 122.8, 130.9, 132.5, 132.6, 141.3, 147.7, 151.9, 152.8, 153.4, 162.6; HRMS-ESI (m/z): [M+H]$^+$, calcd for C$_{21}$H$_{19}$O$_9$S$_2$, 479.0465. found, 479.0472.

The synthesis of carbamate 14 was carried out in an analogous manner to carbonate 13 using 6 in the presence of 4-(dimethylamino)pyridine. $^1$H NMR (500 MHz, CDCl$_3$) δ 2.17 (dd, J=5.2, 1.8 Hz, 1H), 2.23 (s, 6H), 2.55 (dd, J=6.0, 1.6 Hz, 1H), 3.07 (m, 1H), 3.20 (dd, J=14.4, 7.8 Hz, 1H), 3.52 (dd, J=14.3, 5.7 Hz, 1H), 4.95 (s, 2H), 7.08 (d, J=9.0 Hz, 2H), 7.07 (d, J=9.2 Hz, 2H), 7.45 (d, J=8.0 Hz, 2H), 7.86 (d, J=8.8 Hz, 2H); $^{13}$C NMR (126 MHz, CDCl$_3$) δ 9.7, 24.4, 24.5, 26.3, 54.7, 62.8, 117.0, 117.6, 121.5, 122.0, 130.9, 132.0, 133.8, 140.6, 152.4, 163.3; HRMS-ESI (m/z): [M+H]$^+$, calcd for C$_{21}$H$_{20}$NO$_8$S$_2$, 478.0625. found, 478.0625.

4-Fluoro-2-(methoxymethoxy)-1-nitrobenzene (15)

5-Fluoro-2-nitrophenol (10 g, 63 mmol, 99%) was dissolved in anhydrous DMF (100 mL) in an oven-dried flask. The solution was stirred under an atmosphere of nitrogen and cooled in an ice-water bath. Sodium hydride (3.0 g, 75 mmol) was added with stirring, after which chloro methylether (5.3 g, 66 mmol) was added dropwise. The resulting mixture was aged at room temperature for 1 h. The reaction was quenched with MeOH, diluted with ether and washed with water and brine. The ether layer was dried over anhydrous Na$_2$SO$_4$ and concentrated in vacuo. Purification of the product by silica gel chromatography (hexanes/EtOAc=1/7) gave the title compound in 88% yield. $^1$H NMR (500 MHz, CDCl$_3$) δ 3.53 (s, 3H), 5.30 (d, J=2.0 Hz, 2H), 6.78 (dd, J=7.3, 9.1 Hz, 1H), 7.06 (dt, J=2.3, 10.4 Hz, 1H), 7.91 (dd, J=6.0, 9.0 Hz, 1H). $^{13}$C NMR (126 MHz, CDCl$_3$) δ 57.0, 95.6, 105.0 (d, J=26.3 Hz), 108.8 (d, J=23.0 Hz), 127.8 (d, J=10.7 Hz), 152.8 (d, J=11.5 Hz), 165.5 (d, J=255.9 Hz). HRMS (FAB) calcd for C$_8$H$_8$FNNaO$_4$ (M+Na$^+$) 224.0330. found 224.0328.

S-(4-(3-(Methoxymethoxy)-4-nitrophenoxy)phenyl) dimethylcarbamothioate (17)

To a round bottom flask was added dimethylcarbamothioate 16 (2.1 g, 11 mmol), compound 15 (2.5 g, 12 mmol), DMF (50 mL) and Cs$_2$CO$_3$ (7.1 g, 22 mmol). The resulting mixture was stirred for 24 h, followed by filtration over silica gel. The solvent was evaporated and the product was purified by silica gel chromatography (hexanes/EtOAc=2/1) to give 17 as a solid in 88% (3.5 g). $^1$H NMR (500 MHz, CDCl$_3$) δ 3.05 (br.

s., 3H), 3.12 (br. s., 3H), 3.53 (s, 3H), 5.28 (s, 2H), 6.61 (ddd, J=0.8, 2.5, 9.1 Hz, 1H), 6.99 (d, J=2.4 Hz, 1H), 7.12-7.05 (m, 2H), 7.56-7.50 (m, 2H), 7.93-7.88 (m, 1H). $^{13}$C NMR (126 MHz, CDCl$_3$) δ 37.1, 37.2, 57.1, 95.5, 107.1, 110.4, 120.5, 125.1, 127.9, 135.7, 137.9, 153.0, 156.1, 162.0, 166.9. HRMS (FAB) calcd for C$_{17}$H$_{19}$N$_2$O$_6$S (M+H$^+$) 379.0958. found 379.0945.

t-Butyl(4-(4-((dimethylcarbamoyl)thio)phenoxy)-2-(methoxymethoxy)phenyl)carbamate (18)

A solution of 17 (2.5 g, 6.6 mmol) in MeOH/H$_2$O (30 mL/15 mL) was treated with iron (1.9 g, 34 mmol) and NH$_4$Cl (0.35 g, 6.5 mmol) and the resulting mixture was heated at reflux for 2 h. The crude reaction mixture was filtered through Celite and the filtrate was concentrated in vacuo. The residue was dissolved in EtOAc and was washed with water. The organic layer was separated and the aqueous layer was washed with EtOAc. The combined organic portions were dried over anhydrous Na$_2$SO$_4$. The solvent was removed under reduced pressure to provide the amine as a solid (1.9 g, 5.5 mmol, 83%). This product was dissolved in MeOH (30 mL), was treated with TEA (0.6 g, 5.9 mmol) and Boc$_2$O (1.9 g, 8.4 mmol, 97%) and was stirred at room temperature for 24 h. The solvent was removed under reduced pressure and the product was purified by silica gel chromatography (hexanes/EtOAc=3/1) to give the title compound (1.9 g, 76%). $^1$H NMR (500 MHz, CDCl$_3$) δ 1.54 (s, 9H), 3.02 (br. s., 3H), 3.08 (br. s., 3H), 3.48 (s, 3H), 5.18 (s, 2H), 6.71 (dd, J=2.6, 8.8 Hz, 1H), 6.90 (d, J=2.6 Hz, 1H), 6.97-6.92 (m, 2H), 7.00 (br. s., 1H), 7.42-7.36 (m, 2H), 8.05 (br. s., 1H). $^{13}$C NMR (126 MHz, CDCl$_3$) δ 28.4, 36.9, 56.5, 80.5, 95.3, 107.2, 113.6, 117.7, 119.3, 121.6, 125.3, 137.4, 146.5, 150.6, 152.9, 159.4, 167.4. HRMS (FAB) calcd for C$_{22}$H$_{29}$N$_2$O$_6$S (M+H$^+$) 449.1741. found 449.1735.

t-Butyl(2-(methoxymethoxy)-4-(4-((oxiran-2-ylmethyl)thio)phenoxy)phenyl)-carbamate (19)

To a solution of compound 18 (0.65 g, 1.5 mmol) in anhydrous MeOH (10 mL) was added potassium hydroxide (0.42 g, 7.5 mmol). The mixture was refluxed for 4 h and then cooled to room temperature. Epichlorohydrin (0.21 g, 2.3 mmol) was added dropwise and the mixture was stirred at room temperature for 15 min, after which the solvent was removed under reduced pressure. The concentrate was diluted with water and extracted with EtOAc. The combined organic extracts were dried over anhydrous Na$_2$SO$_4$, the suspension was filtered, followed by concentration of the filtrate in vacuo. Purification by silica gel chromatography (hexanes/EtOAc=4/1) gave 19 in 68% yield (0.43 g) $^1$H NMR (500 MHz, CDCl$_3$) δ 1.53 (s, 9H), 8.03 (br. s., 1H), 2.47 (dd, J=2.6, 5.0 Hz, 1H), 2.77 (t, J=4.4 Hz, 1H), 2.85 (dd, J=6.1, 13.9 Hz, 1H), 3.12-3.05 (m, 1H), 3.18-3.12 (m, 1H), 5.18 (s, 2H), 3.48 (s, 3H), 6.66 (dd, J=2.6, 8.8 Hz, 1H), 6.92-6.85 (m, 3H), 6.98 (br. s., 1H), 7.44-7.37 (m, 2H). $^{13}$C NMR (126 MHz, CDCl$_3$) δ 28.5, 38.2, 47.6, 51.3, 56.5, 80.6, 95.4, 106.8, 113.1, 118.4, 119.4, 125.1, 128.0, 131.8, 133.8, 146.6, 151.2, 152.9, 157.9. HRMS (FAB) calcd for C$_{22}$H$_{28}$NO$_4$S (M+H$^+$) 434.1632. found 434.1637.

t-Butyl(2-(methoxymethoxy)-4-(4-((oxiran-2-ylmethyl)sulfonyl)phenoxy)phenyl)-carbamate (20)

Compound 19 (0.44 g, 1.0 mmol) was dissolved in CH$_2$Cl$_2$ (10 ml) and cooled in an ice-water bath. It was treated with m-CPBA (0.48 g, 2.1 mmol, 77%) and the resulting white suspension was stirred at room temperature for 10 min. The mixture was filtered and the filtrate was washed with saturated Na$_2$S$_2$O$_3$, followed by saturated NaHCO$_3$. The organic layer was separated and the aqueous layer was washed with CH$_2$Cl$_2$. The combined organic solution was dried over anhydrous Na$_2$SO$_4$, the suspension was filtered and the filtrate was concentrated in vacuo. Purification of the product by silica gel chromatography (hexanes/EtOAc=2/1) gave the title compound in 89% yield (0.42 g). $^1$H NMR (500 MHz, CDCl$_3$) δ 1.54 (s, 9H), 2.48 (dd, J=2.2, 4.8 Hz, 1H), 2.82 (t, J=4.5 Hz, 1H), 3.28-3.19 (m, 1H), 3.38-3.28 (m, 2H), 3.49 (s, 3H), 5.20 (s, 2H), 6.73 (dd, J=2.6, 8.8 Hz, 1H), 6.91 (d, J=2.6 Hz, 1H), 7.03 (s, 1H), 7.09-7.04 (m, 2H), 7.89-7.83 (m, 2H), 8.13 (br. s., 1H). $^{13}$C NMR (126 MHz, CDCl$_3$) δ 28.5, 46.0, 46.1, 56.6, 59.8, 80.9, 95.4, 107.5, 114.2, 117.2, 119.5, 126.3, 130.6, 132.3, 146.7, 149.4, 152.9, 163.5. HRMS (FAB) calcd for C$_{22}$H$_{28}$NO$_8$S (M+H$^+$) 466.1530. found 466.1543.

t-Butyl(2-(methoxymethoxy)-4-(4-((thiiran-2-ylmethyl)sulfonyl)phenoxy)phenyl)carbamate (21)

To a solution of 20 (0.40 g, 0.86 mmol) in CH$_2$Cl$_2$ (5 mL) was added a mixture of thiourea (0.10 g, 1.3 mmol, 99%) in methanol (5 mL). The resulting mixture was stirred for 24 h at room temperature, after which the solvent was removed under reduced pressure. The residue was partitioned between CH$_2$Cl$_2$ and water. The organic layer was dried over anhydrous Na$_2$SO$_4$ and was filtered. Evaporation of solvent and purification by silica gel chromatography (hexanes/EtOAc=4/1) gave 0.34 g of 21 (83%). $^1$H NMR (500 MHz, CDCl$_3$) δ 1.53 (s, 9H), 2.14 (dd, J=1.8, 5.0 Hz, 1H), 2.52 (dd, J=1.5, 5.9 Hz, 1H), 3.04 (dq, J=5.6, 7.8 Hz, 1H), 3.15 (dd, J=8.0, 14.2 Hz, 1H), 3.47 (s, 3H), 3.51 (dd, J=5.6, 14.4 Hz, 1H), 5.19 (s, 2H), 6.72 (dd, J=2.6, 8.8 Hz, 1H), 6.91 (d, J=2.6 Hz, 1H), 7.08-7.01 (m, 3H), 7.85-7.80 (m, 2H), 8.16-8.08 (m, 1H). $^{13}$C NMR (126 MHz, CDCl$_3$) δ 24.4, 26.2, 28.5, 56.6, 62.7, 80.8, 95.3, 107.3, 114.1, 117.3, 119.4, 126.2, 130.8, 131.6, 146.6, 149.3, 152.8, 163.5. HRMS (FAB) calcd for C$_{22}$H$_{28}$NO$_7$S$_2$ (M+H$^+$) 482.1302. found 482.1301.

2-Amino-5-(4-((thiiran-2-ylmethyl)sulfonyl)phenoxy)phenol (22)

To a solution of compound 21 (0.10 mg, 0.21 mmol) in methanol (5 mL) was added a few drops of conc. HCl. After the mixture was stirred at reflux for 1 h, the solvent was evaporated in vacuo. The crude product was taken up into water and EtOAc. Layers were separated and the aqueous layer was washed with EtOAc. The combined organic layers were dried over anhydrous Na$_2$SO$_4$, the suspension was filtered and the filtrate was concentrated in vacuo. Purification by silica gel chromatography (hexanes/EtOAc=1/1) gave 22 in 95% yield (66 mg). $^1$H NMR (500 MHz, CDCl$_3$) δ2.14 (dd, J=1.3, 4.9 Hz, 1H), 2.18 (d, J=1.0 Hz, 1H), 2.56-2.49 (m, 1H), 3.08-3.00 (m, 1H), 3.17 (dd, J=7.8, 14.4 Hz, 1H), 3.51 (dd, J=5.6, 14.2 Hz, 2H), 6.54-6.46 (m, 2H), 6.80-6.73 (m, 1H), 7.07-6.97 (m, 2H), 7.80 (m, 2H). $^{13}$C NMR (126 MHz, CDCl$_3$) δ 24.4, 26.3, 62.8, 108.5, 113.1, 117.2, 117.9, 130.7, 131.1, 131.9, 145.9, 147.3, 164.1. HRMS (FAB) calcd for C$_{15}$H$_{16}$NO$_4$S$_2$ (M+H$^+$) 338.0515. found 338.0507.

Example 2

Experimental Inhibition Data

Fluorescence Enzymatic Activity Assays.

The enzymatic activity of MMP-2, MMP-9, and MMP-7 was monitored with the fluorescence quenched substrate MOCAcPLGLA$_2$pr(Dnp)-AR-NH$_2$. Fluorescence was measured with a Photon Technology International (PTI) spectrofluorometer interfaced to a Pentium computer, equipped with the RatioMaster™ and FeliX™ hardware and software, respectively. The cuvette compartment was thermostated at 25° C. Substrate hydrolysis was monitored at emission and excitation wavelengths of 328 and 393 nm and excitation and emission band passes of 1 and 3 nm, respectively. Fluorescence measurements were taken every 4 seconds. Less than 10% hydrolysis of the fluorogenic substrate was monitored, as described by Knight. Knight, C. G. *Methods Enzymol.* 1995, 248, 18-34. Stromelysin 1 enzymatic activity was monitored using the synthetic fluorogenic substrate MOCAcRPKPVE-Nva-WRK(Dnp)-NH$_2$ (Peptides International, Louisville, Ky.) at excitation and emission wavelengths of 325 and 393 nm and excitation and emission band passes of 1 and 3 nm, respectively.

The following buffers were used in experiments with enzymes: Buffer C (50 mM HEPES at pH 7.5, 150 mM NaCl, 5 mM CaCl$_2$, 0.02% Brij-35); buffer R (50 mM HEPES at pH 7.5, 150 mM NaCl, 5 mM CaCl$_2$, 0.01% Brij-35, and 1% v/v Me$_2$SO) and buffer D (50 mM Tris at pH 7.5, 150 mM NaCl, 5 mM CaCl$_2$, and 0.02% Brij-35).

Enzymes and Protein Inhibitors.

Human pro-MMP-2, pro-MMP-9, TIMP-1 and TIMP-2 were expressed in HeLa S3 cells infected with the appropriate recombinant vaccinia viruses and were purified to homogeneity, as previously described. See Fridman et al., *J. Biol. Chem.* 1992, 267, 15398-15405 and Fridman et al., *Biochem. J.* 1993, 289, 411-416. Pro-MMP-2, pro-MMP-9, TIMP-1 and TIMP-2 concentrations were determined using the extinction coefficients of 122,800, 114,360, 26,500 and 39,600 M$^{-1}$ cm$^{-1}$, respectively. To obtain active MMP-2, pro-MMP-2 (7.3 μM) was incubated at 37° C. for 1 h with 1 mM p-aminophenyl-mercuric acetate (APMA) (dissolved in 200 mM Tris) in buffer C. The enzyme solution was dialyzed against buffer D at 4° C. to remove APMA. Active MMP-9 was obtained by incubating pro-MMP-9 (1 μM) with heat-activated recombinant human stromelysin 1 (68 nM) (MMP-3, generously provided by Dr. Paul Cannon, Center for Bone and Joint Research, Palo Alto, Calif.) at 37° C., for 2.5 h in buffer C.

The resulting solution was subjected to gelatin-agarose chromatography to remove stromelysin 1. MMP-9 was eluted with buffer D containing 10% DMSO and dialyzed against the same buffer without DMSO to remove the organic solvent. Pro-MMP-2 and pro-MMP-9 activation reactions were monitored using the fluorescence quenched substrate MOCAcPLGLA$_2$pr(Dnp)-AR—NH$_2$ (Peptides International, Louisville, Ky.; PLGLAAAR), as will be described below. The MMP-2 and MMP-9 concentrations were determined by titration with TIMP-1.

Kinetic Analyses.

Progress curves were obtained by adding enzyme (0.5-2 nM) to a mixture of fluorogenic substrate (5-7 μM) and varying concentrations of inhibitor in buffer R containing 5-15% DMSO (final volume 2 ml), in acrylic cuvettes with stirring and monitoring the increase in fluorescence with time for 15-30 minutes. The progress curves were nonlinear least squares fitted to Equation 1 (Muller-Steffner et al., *J. Biol. Chem.* 1992, 267, 9606-9611):

$$F = v_s t + I(v_o - v_s)(1 - \exp(-kt))/k + F_0 \qquad (1)$$

where $v_o$ represents the initial rate, $v_s$, the steady state rate, k, the apparent first order rate constant characterizing the formation of the steady-state enzyme-inhibitor complex and $F_o$, the initial fluorescence, using the program SCIENTIST (MicroMath Scientific Software, Salt Lake City, Utah). The obtained k values, $v_0$ and $v_s$ were further analyzed according to Equations 2 and 3 for a one-step association mechanism:

$$k = k_{off} + k_{on}[I]/(1 + [S]/K_m) \qquad (2)$$

$$(v_o - v_s)/v_s = [I]/(K_i(1 + [S]/K_m)) \qquad (3)$$

Intercept and slope values, obtained by linear regression of the k versus inhibitor concentration plot (Equation 2), yielded the association and dissociation rate constants $k_{on}$ and $k_{off}$, respectively, and the inhibition constant $K_i$ ($k_{off}/k_{on}$). Alternatively, $K_i$ was determined from the slope of the $(v_o - v_s)/v_s$ vs [I] plot according to Equation 3.

The dissociation rate constants were determined independently from the enzyme activity recovered after dilution of a pre-formed enzyme-inhibitor complex. To this end, typically 200 nM of enzyme was incubated with 1 μM of inhibitor for a sufficient time to reach equilibrium (>45 min) at 25.0° C. The complex was diluted into 2 mL of buffer R containing fluorogenic substrate (5-7 μM final concentration) to a final enzyme concentration of 1 nM. Recovery of enzyme activity was monitored for ~30 min. The fluorescence versus time trace was fitted, using the program SCIENTIST, to Equation 4:

$$F = v_s t + (v_o - vs)(1 - \exp(-k_{off}))/k_{off} + F_0 \qquad (4)$$

where $v_o$ represents the initial rate (very small), $v_s$, the rate observed when the E.I complex is completely dissociated and $k_{off}$, the first order rate constant when the E.I dissociation.

Analysis for linear competitive inhibition was performed in the following manner. Initial rates were obtained by adding enzyme (0.5-2 nM) to a mixture of fluorogenic substrate (5-7 μM) and varying concentrations of inhibitor in buffer R, containing 5-15% DMSO (final volume 1 mL) in semi-micro quartz cuvettes, and monitoring the increase in fluorescence with time for 5-10 minutes. The fluorescence versus time traces were fitted by linear regression analysis using FeliX™. The initial rates were fitted to Equation 5 (Segel, I. H. in: *Enzyme Kinetics*, Wiley Inc., New York, 1975, pp. 104):

$$v/V_{max} = S/(K_m(1 + I/K_i) + S) \qquad (5)$$

where v and $V_{max}$ represent the initial and maximal velocities, S and I, the substrate and inhibitor concentrations, respectively, $K_m$ the Michaelis-Menten constant for the substrate-enzyme reaction and $K_i$ the inhibition constant, using the program SCIENTIST.

TABLE 2

Inhibition Data of Certain Specific Compounds.

| Cmpd. | MMP-2 | MMP-9 | Water Solubility | Half-life in human plasma at 37° C. (min) | Half-life in human blood at 37° C. (min) |
|---|---|---|---|---|---|
| 11a | [1]$k_{on}$: 1.9 ± 0.6<br>[2]$k_{off}$: 8.2 ± 0.9<br>[3]$K_i$: 0.44 ± 0.05 | $k_{on}$: 0.21 ± 0.04<br>$k_{off}$: 6.5 ± 0.6<br>$K_i$: 3.1 ± 0.3 | >10 mg/mL | 32.4 ± 2.7 | 27.1 ± 2.5 |
| 11b | $k_{on}$: 3.4 ± 0.1<br>$k_{off}$: 2.1 ± 0.9<br>$K_i$: 0.062 ± 0.025 | $k_{on}$: 0.27 ± 0.04<br>$k_{off}$: 4.2 ± 0.7<br>$K_i$: 1.6 ± 0.3 | >10 mg/mL | 25.1 ± 5.2 | 15.3 ± 1.9 |
| 11c | $k_{on}$: 2.5 ± 0.1<br>$k_{off}$: 1.8 ± 1.6<br>$K_i$: 0.069 ± 0.064 | $k_{on}$: 2.3 ± 0.1<br>$k_{off}$: 12.0 ± 0.7<br>$K_i$: 5.4 ± 0.3 | >10 mg/mL | 32.8 ± 3.6 | 27.9 ± 3.8 |
| 11d | $k_{on}$: 7.6 ± 2.9<br>$k_{off}$: 1.5 ± 0.1<br>$K_i$: 0.52 ± 0.20 | $k_{on}$: 0.031 ± 0.006<br>$k_{off}$: 6.0 ± 0.3<br>$K_i$: 19.6 ± 1.0 | >10 mg/mL | 29.5 ± 0.7 | 25.4 ± 0.1 |
| 11e | $k_{on}$: 1.5 ± 0.1<br>$k_{off}$: 6.1 ± 2.1<br>$K_i$: 0.42 ± 0.15 | $k_{on}$: 0.044 ± 0.004<br>$k_{off}$: 8.3 ± 2.3<br>$K_i$: 18.7 ± 5.6 | >10 mg/mL | 11.8 ± 0.5 | 5.9 ± 0.6 |
| 14 | $K_i$: 2.4 ± 0.6 | 37% inhibition at 80 μM | *1.01 (±0.02) μg/mL | 1.6 ± 0.4 | |

[1]$k_{on}$: ×10$^3$ M$^{-1}$ s$^{-1}$
[2]$k_{off}$: ×10$^{-4}$ s$^{-1}$
[3]$K_i$: in μM
*in 100% water; solubility calculated using ε of MIK-G6 (p-N-acetyl SB-3CT)

TABLE 3

Kinetic Parameters for Inhibition of MMPs by Compounds 11d, 6, and 22.

| Compound | MMP | $k_{on}$: ×10$^3$ M$^{-1}$ s$^{-1}$ | $k_{off}$: ×10$^{-4}$ s$^{-1}$ | $K_i$: in μM |
|---|---|---|---|---|
| 11d | MMP-2 | 7.6 ± 2.9 | 1.5 ± 0.1 | 0.52 ± 0.20 |
|  | MMP-9 | 0.031 ± 0.006 | 6.0 ± 0.3 | 19.6 ± 1.0 |
|  | MMP-1 | — | — | 43% inhibition at 1 mM |
|  | MMP-3 | — | — | 40.5 ± 1.2 |
|  | MMP-7 | — | — | 160 ± 14 |
|  | MMP-14 | 0.42 ± 0.01 | 12.0 ± 0.1 | 28.9 ± 2.3 |
| 6 | MMP-2 | 8.9 ± 0.2 | 2.1 ± 1.3 | 0.024 ± 0.015 |
|  | MMP-9 | 0.61 ± 0.01 | 5.3 ± 0.7 | 0.87 ± 0.11 |
|  | MMP-1 | — | — | No inhibition at 20 μM |
| 6 | MMP-3 | — | — | 3% inhibition at 20 μM |
|  | MMP-7 | — | — | No inhibition at 200 μM |
|  | MMP-14 | 8.0 ± 0.4 | 8.0 ± 0.3 | 0.1 ± 0.006 |
| 22 | MMP-2 | 1.7 ± 0.1 | 1.4 ± 0.7 | 0.078 ± 0.043 |
|  | MMP-9 | 1.07 ± 0.12 | 5.3 ± 1.0 | 0.49 ± 0.11 |
|  | MMP-1 | — | — | 11% inhibition at 300 μM |
|  | MMP-3 | — | — | 54% inhibition at 300 μM |
|  | MMP-7 | — | — | 116 ± 13 |
|  | MMP-14 | 2.69 ± 0.27 | 7.02 ± 1.61 | 0.26 ± 0.07 |

TABLE 4

Half-lives in Liver Microsomes.

| Compound | Half-life in min | | |
|---|---|---|---|
|  | Mouse | Rat | Human |
| 11d | >60 | 59.3 ± 4.5 | >60 |
| 6 | 27.3 ± 2.1 | 23.4 ± 0.7 | >60 |

As can be observed from the data above, the compounds described herein have significantly improved solubilities over SB-3CT and convert to the active compound 6 in human blood and plasma within 30 minutes. The methods used to obtain the data of Table 2 are known in the art and are described, for example, by Brown et al., *J. Amer. Chem. Soc.* 2000, 122(28), 6799-6800, and the references cited therein. Additional useful assays and techniques are described in U.S. Patent Publication No. 2009/0209615 (Lipton et al.), which is incorporated herein by reference in its entirety. Compound 11d was evaluated for its mutagenic potential by measuring its ability to induce reverse mutations at selected loci of Ames II mixed strains and strain TA98 in the presence and absence of rat liver S9 metabolic activation at six concentrations up to 1 mg/mL (equivalent to 300 μM). Compound 11d was negative (non-mutagenic) in this Ames mutagenicity assay with and without metabolic activation.

Example 3

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of treating a disease or condition that is modulated by a matrix metalloproteinase (MMP) comprising administering to a patient in need of such treatment an effective amount of a compound of Formula A:

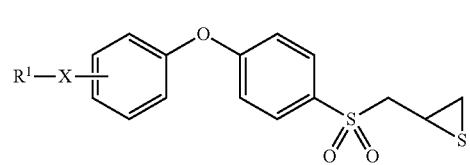

(A)

wherein X is O, NH or —S—NH—, and $R^1$ is:

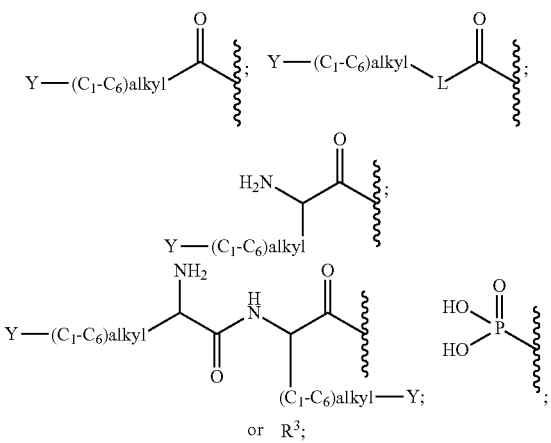

or $R^3$;

wherein

L is O, NH, —OCH$_2$O—, or —C(=O)O—CH$_2$O—;

each Y is independently —NH$_2$, —CO$_2$H, —P(=O)(OH)$_2$, —OP(=O)(OH)$_2$, Het, or a guanidine moiety;

Het is a 5 or 6 membered heterocyclic ring comprising 1, 2, or 3 heteroatoms selected from O, N, S, or P, wherein the ring optionally includes one or two sites of unsaturation and the ring is optionally substituted with 1, 2, or 3 oxo, halo, nitro, or methyl groups; and R³ is an amino acid or a linear or branched chain of two to five amino acids, linked to X or the carbonyl of R¹ by a nitrogen or sulfur atom;

or a salt thereof; wherein the compound has an aqueous solubility of at least 5 mg/mL;

thereby treating the disease or condition.

2. The method of claim 1 wherein each $(C_1$-$C_6)$alkyl is independently —$(CH_2)$—, —$(CH_2)_2$—, —$(CH_2)_3$—, —$(CH_2)_4$—, or —$(CH_2)_5$—.

3. The method of claim 1 wherein R¹—X— is meta or para with respect to the oxygen of the phenoxy moiety to which it is attached.

4. The method of claim 1 wherein the compound of Formula A is a gelatinase inhibitor that has a water solubility that is at least 5000-fold greater than SB-3CT.

5. The method of claim 1 wherein the compound of Formula A inhibits MMP-2 and has a $K_i$ of less than 3 μM.

6. The method of claim 1 wherein the compound of Formula A inhibits MMP-9 and has a $K_i$ of less than 20 μM.

7. The method of claim 1 wherein the matrix metalloproteinase (MMP) is a gelatinase, a collagenase, a stromelysin, MMP-19, MMP-23, or matrilysin, and the activity of the matrix metalloproteinase is inhibited.

8. The method of claim 7 wherein the disease or condition is cancer, stroke, a chronic wound, an ophthalmological disorder, traumatic brain injury, or spinal cord injury.

9. The method of claim 8 wherein the condition is stroke, and the stroke is ischemic stroke or hemorrhagic stroke.

10. The method of claim 1 wherein administering a compound of Formula A is carried out in combination with administering a thrombolytic agent.

11. The method of claim 10 wherein the thrombolytic agent is a tissue plasminogen activator, reteplase, urokinase, prourokinase, anisoylated purified streptokinase activator complex (APSAC), or streptokinase.

12. A method of treating a disease or condition that is modulated by a matrix metalloproteinase (MMP) comprising administering to a patient in need of such treatment an effective amount of a compound of Formula I:

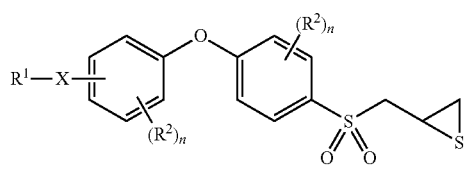

(I)

wherein
X is O, NR$^a$, or —S—NH—;
R$^a$ is H or $(C_1$-$C_4)$alkyl;
R¹ is —(C=O)-L-$(CH_2)_{(m-1)}$—$CH_3$, —(C=O)—$(CH_2)_m$—Y; —(C=O)-L-$(CH_2)_m$—Y; —(C=O)—(CHR$^x$)—NHR$^y$; —P(=O)(OH)$_2$; an amino acid; or a linear or branched chain of two to five amino acids;
L is O, NH, —OCH$_2$O—, or —C(=O)O—CH$_2$O—;
R$^x$ is H or —$(CH_2)_m$Y;
R$^y$ is H or —(C=O)—CH(NH$_2$)—$(CH_2)_m$Y;
m is 1-6;
each Y is independently —NH$_2$, —CO$_2$H, —P(=O)(OH)$_2$, —OP(=O)(OH)$_2$, Het, or a guanidine moiety;

Het is a 5 or 6 membered heterocyclic ring comprising 1, 2, or 3 heteroatoms selected from O, N, S, or P, wherein the ring optionally includes one or two sites of unsaturation and the ring is optionally substituted with 1, 2, or 3 oxo, halo, nitro, or methyl groups;

each R² is independently hydroxy, $(C_1$-$C_6)$alkyl, $(C_1$-$C_6)$alkoxy, $(C_1$-$C_6)$alkanoyl, $(C_1$-$C_6)$alkanoyloxy, aryl, heteroaryl, carboxy, cyano, nitro, halo, trifluoromethyl, trifluoromethoxy, SR$^z$, SO$_2$N(R$^z$)$_2$, NR$^z$R$^z$, or COOR$^z$; wherein each R$^z$ is independently H, $(C_1$-$C_6)$alkyl, $(C_1$-$C_6)$alkanoyl, $(C_6$-$C_{10})$aroyl, aryl, aryl$(C_1$-$C_6)$alkyl, heteroaryl, heteroaryl$(C_1$-$C_6)$alkyl, or optionally a nitrogen protecting group when covalently bonded to a nitrogen atom; and each n is independently 0, 1, 2, 3, or 4;

or a salt thereof; and wherein the compound has an aqueous solubility of at least 5 mM;

thereby treating the disease or condition.

13. The method of claim 12 wherein X is O or NH, n is 0, and R¹ is:

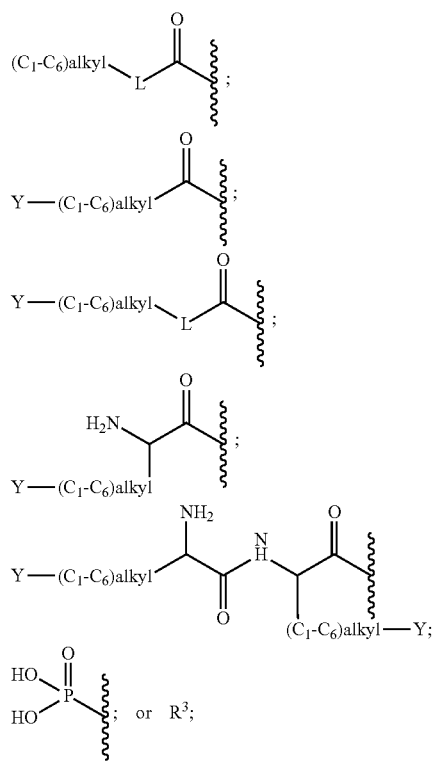

wherein
L is O, NH, —OCH$_2$O—, or —C(=O)O—CH$_2$O—;
R³ is an amino acid or a linear or branched chain of two to five amino acids, linked to X by a carbonyl or sulfur residue;

or a salt thereof.

14. The method of claim 12 wherein each $(C_1$-$C_6)$alkyl is independently —$(CH_2)$—, —$(CH_2)_2$—, —$(CH_2)_3$—, —$(CH_2)_4$—, or —$(CH_2)_5$—.

15. The method of claim 12 wherein the compound of Formula I is:

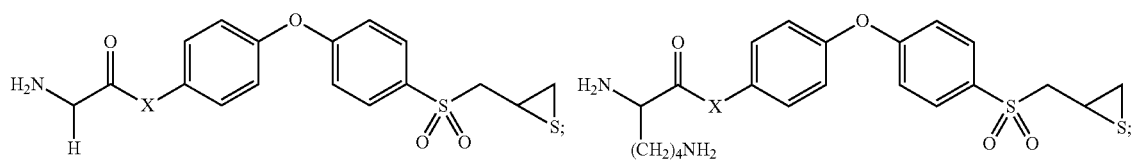
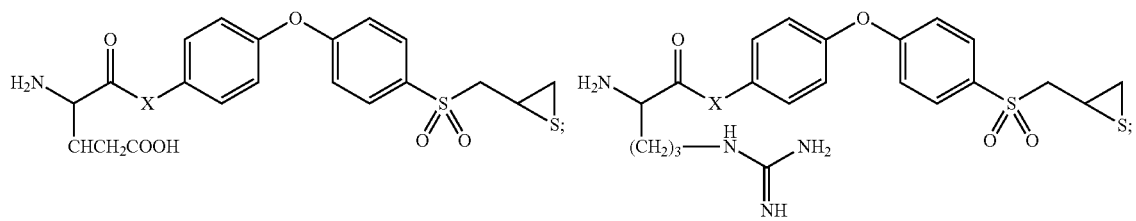
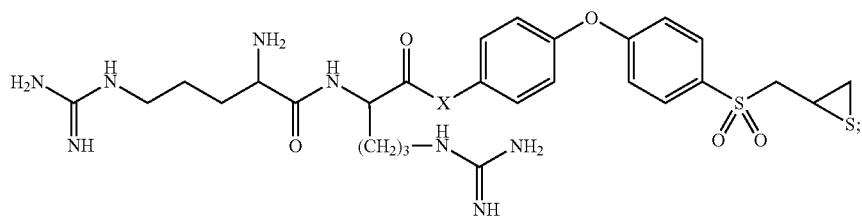
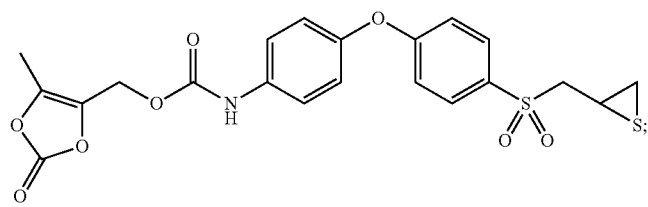
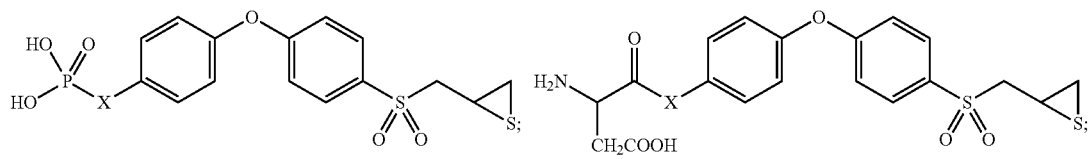
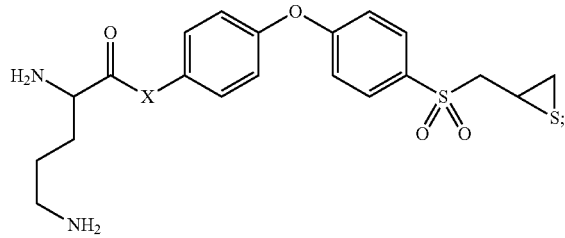
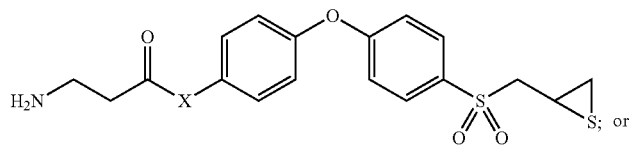
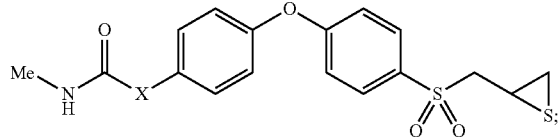
wherein X is O or NH;
or a salt thereof.
16. The method of claim 12 wherein the compound of Formula I is a compound of Formula II or Formula III:

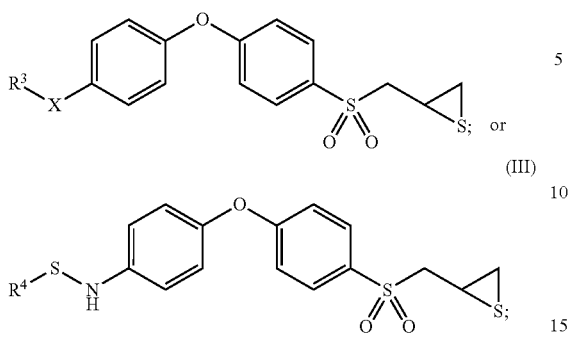

wherein
X is O or NH;
R³ is an amino acid moiety selected from Ala, Cys, Asp, Glu, Phe, Gly, His, Ile, Lys, Leu, Met, Asn, Pro, Gln, Arg, Ser, Thr, Val, Trp, or Tyr, optionally protected on any nitrogen, sulfur, or carboxylic acid with a protecting group, or a non-natural amino acid selected from phosphoserine; phosphothreonine; phosphotyrosine; hydroxyproline; γ-carboxyglutamate; hippuric acid; octahydroindole-2-carboxylic acid; statine; 1,2,3,4,-tetrahydroisoquinoline-3-carboxylic acid; penicillamine; ornithine; citrulline; α-methyl-alanine; para-benzoyl-phenylalanine; phenylglycine; propargylglycine; sarcosine; and tert-butylglycine; or R³ is a combination of any two to five amino acids in a linear or branched configuration; and
R⁴ is a residue of a sulfur-containing amino acid linked to Formula III by its sulfur atom shown as part of Formula III;
or a salt thereof.

17. The method of claim 12 wherein the compound of Formula I is:

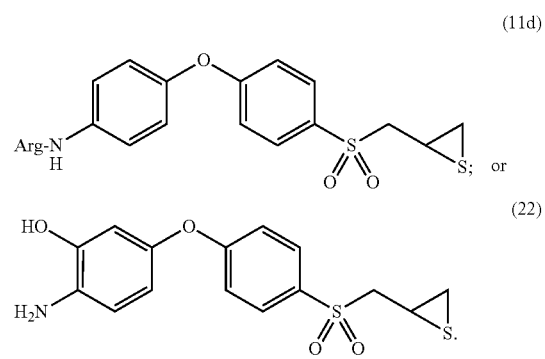

18. The method of claim 12 wherein the compound of Formula I is formulated as a pharmaceutical composition for intravenous, subcutaneous, intracardiac, intramuscular, intraperatoneal, or topical administration.

19. The method of claim 12 wherein the compound of Formula I is a gelatinase inhibitor that has a water solubility that is at least 5000-fold greater than SB-3CT.

20. The method of claim 12 wherein the matrix metalloproteinase (MMP) is a gelatinase, a collagenase, a stromelysin, MMP-19, MMP-23, or matrilysin, and the activity of the matrix metalloproteinase is inhibited.

21. The method of claim 20 wherein the disease or condition is cancer, stroke, a chronic wound, an ophthalmological disorder, traumatic brain injury, or spinal cord injury.

* * * * *